United States Patent
Schuele

(10) Patent No.: US 11,096,680 B2
(45) Date of Patent: Aug. 24, 2021

(54) SURGICAL RETRACTOR SYSTEM AND METHOD

(71) Applicant: pro med instruments GmbH, Freiburg im Breisgau (DE)

(72) Inventor: Matthias E. Schuele, Freiburg (DE)

(73) Assignee: pro med instruments GmbH, Freiburg im Breisgau (DE)

( * ) Notice: Subject to any disclaimer, the term of this patent is extended or adjusted under 35 U.S.C. 154(b) by 1057 days.

(21) Appl. No.: 14/566,800

(22) Filed: Dec. 11, 2014

(65) Prior Publication Data
US 2015/0157306 A1 Jun. 11, 2015

Related U.S. Application Data

(60) Provisional application No. 61/914,939, filed on Dec. 11, 2013.

(51) Int. Cl.
*A61B 90/14* (2016.01)
*A61B 17/02* (2006.01)
(Continued)

(52) U.S. Cl.
CPC .... *A61B 17/02* (2013.01); *A61B 2017/00314* (2013.01); *A61B 2017/00477* (2013.01); *A61B 2090/101* (2016.02); *A61B 2090/571* (2016.02)

(58) Field of Classification Search
CPC .......... A61B 17/02; A61B 2017/00314; A61B 2017/00477; A61B 2090/571;
(Continued)

(56) References Cited

U.S. PATENT DOCUMENTS 5,772,583 A 6/1998 Wright et al.
5,888,197 A 3/1999 Mulac et al.
(Continued)

FOREIGN PATENT DOCUMENTS

CN 2382366 Y 6/2000
CN 101015466 A 8/2007
(Continued)

OTHER PUBLICATIONS

International Search Report and Written Opinion dated Jun. 1, 2015 for Application No. PCT/IB2014/003148.
(Continued)

*Primary Examiner* — Samuel S Hanna
(74) *Attorney, Agent, or Firm* — Frost Brown Todd LLC

(57) ABSTRACT

A retractor system for use in medical procedures is connectable to a head fixation device. The retractor system includes a support assembly and an accessory that is mountable thereto. The support assembly is coupled with the head fixation device such that a position of the support assembly is adjustable relative to the head fixation device. The support assembly includes an upright support and a rod having a non-circular profile. The support assembly and rod are selectively and adjustably coupled to one another via a coupling assembly. The coupling assembly includes a pair of resilient members having contacting and non-contacting surfaces within bores of the resilient members. The accessory and rod are selectively and adjustably coupled to one another via another coupling assembly that comprises locking features operable to selectively engage and disengage the accessory with the rod.

15 Claims, 15 Drawing Sheets

(51) Int. Cl.
*A61B 17/00* (2006.01)
*A61B 90/10* (2016.01)
*A61B 90/57* (2016.01)

(58) Field of Classification Search
CPC .............. A61B 90/14; A61B 10/0233; A61B 2017/3407; A61B 90/11
See application file for complete search history.

(56) References Cited

U.S. PATENT DOCUMENTS

| | | | |
|---|---|---|---|
| 5,897,087 | A | 4/1999 | Farley |
| 6,033,363 | A | 3/2000 | Farley et al. |
| 7,473,223 | B2 | 1/2009 | Fetzer |
| 8,100,827 | B2 | 1/2012 | Farley |
| 8,617,064 | B2 | 12/2013 | Farley |
| 8,696,668 | B2 | 4/2014 | Winquist et al. |
| 9,615,733 | B2 | 4/2017 | Nottmeier |
| 2002/0151892 | A1* | 10/2002 | Walulik ............... A61B 17/645 606/57 |
| 2002/0165543 | A1* | 11/2002 | Winquist ........... A61B 17/6466 606/54 |
| 2005/0080319 | A1* | 4/2005 | Dinkler, II ......... A61B 17/0293 600/201 |
| 2006/0084900 | A1* | 4/2006 | Schule ................... A61B 90/50 602/36 |
| 2006/0229602 | A1* | 10/2006 | Olsen ................ A61B 17/6416 606/54 |
| 2006/0265074 | A1* | 11/2006 | Krishna ............. A61B 17/7011 623/17.15 |
| 2007/0049932 | A1* | 3/2007 | Richelsoph .......... A61B 17/645 606/252 |
| 2007/0213597 | A1 | 9/2007 | Wooster |
| 2008/0071145 | A1 | 3/2008 | Bjork et al. |
| 2013/0204091 | A1 | 8/2013 | Menendez et al. |
| 2014/0066931 | A1* | 3/2014 | Myers ................ A61B 17/6458 606/59 |
| 2014/0135765 | A1 | 5/2014 | Schuele et al. |
| 2014/0275799 | A1 | 9/2014 | Schuele |

FOREIGN PATENT DOCUMENTS

| | | |
|---|---|---|
| CN | 101505677 A | 8/2009 |
| CN | 201578295 U | 9/2010 |
| CN | 102018555 A | 4/2011 |
| CN | 202376161 U | 8/2012 |
| CN | 103260535 A | 8/2013 |
| JP | S58-159736 A | 9/1983 |
| JP | S63-50308 U | 4/1988 |
| JP | 2000-227179 A | 8/2000 |
| JP | 2005-523744 A | 8/2005 |
| JP | 2006-204958 A | 8/2006 |
| WO | WO 99/04681 | 2/1999 |

OTHER PUBLICATIONS

Japanese Office Action, Notice of Reasons for Refusal, dated Sep. 4, 2020 for Application No. JP 2016-537552, Appeal No. 2019-14729, 5 pgs.
Japanese Office Action, Notification of Reasons for Refusal, dated Aug. 16, 2018 for Application No. JP 2016-537552, 8 pgs.
Japanese Search Report dated Aug. 14, 2018 for Application No. JP 2016-537552, 27 pgs.
Chinese Office Action, The Second Office Action, dated Oct. 31, 2018 for Application No. CN 201480066853.3, 20 pgs.
Japanese Office Action, Decision of Refusal, dated Jul. 2, 2019 for Application No. JP 2016-537552, 3 pgs.
Japanese Office Action, Reconsideration Report by Examiner before Appeal, dated Feb. 13, 2020 for Application No. JP 2016-537552, Appeal No. JP 2019-014729, 3 pgs.

* cited by examiner

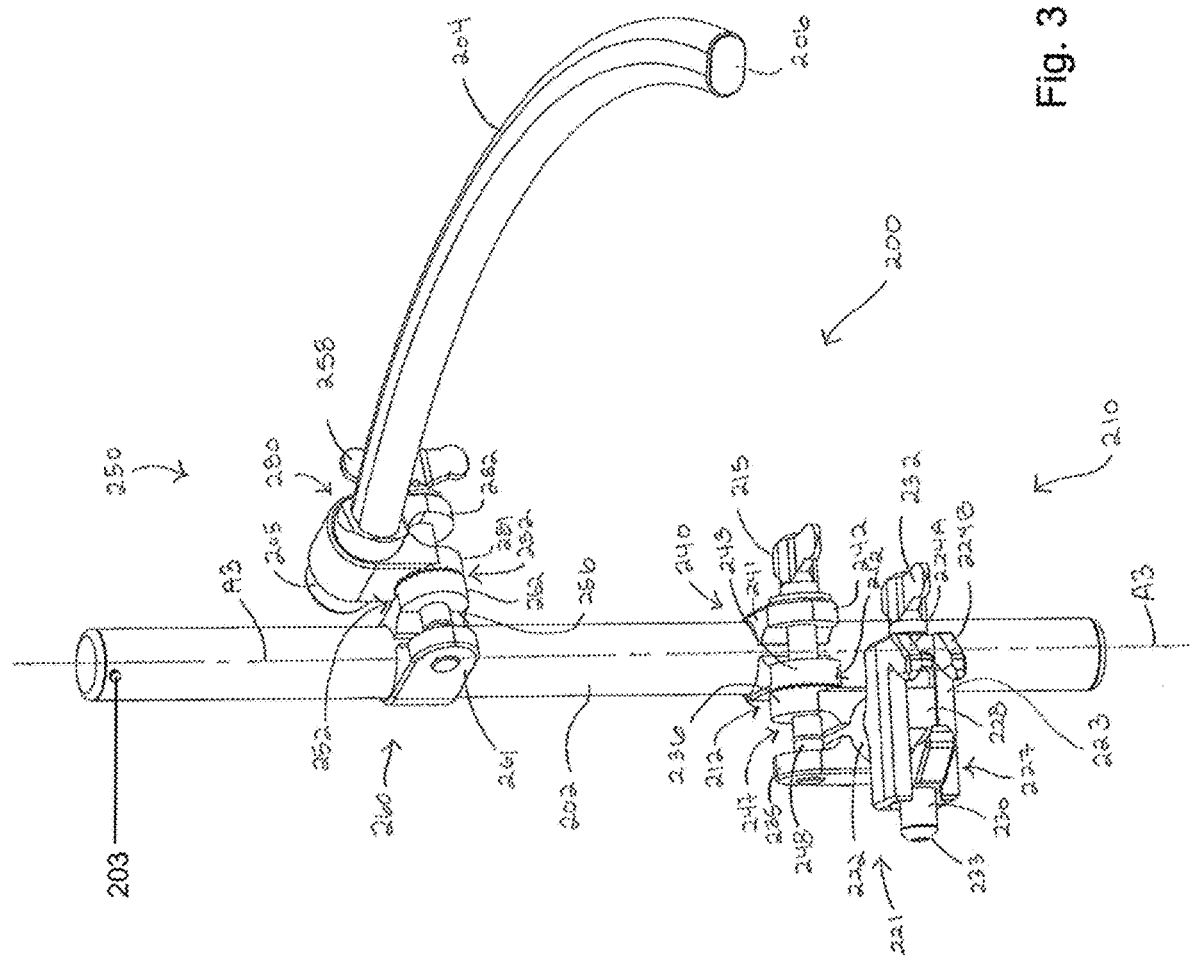

SURGICAL RETRACTOR SYSTEM AND METHOD

PRIORITY

This application claims priority to U.S. Provisional Patent Application Ser. No. 61/914,939, filed Dec. 11, 2013, entitled "Surgical Retractor System and Method," the disclosure of which is incorporated by reference herein.

BACKGROUND

Surgical retractor systems can be used in certain medical procedures where retraction, holding, or positioning of tissue, for example, would be beneficial. One type of surgical retractor system can have application in head and/or neck procedures, although retractor systems can be used with other procedures as well. Retractor systems can be used with other components or devices, and in some instances retractor systems can be attached to such other components or devices. For example, in some instances a retractor system can be attached to a surgical table. In other instances a retractor system can be attached to a head fixation device, such as a halo or skull clamp.

While a variety of surgical retractor systems, have been made and used, it is believed that no one prior to the inventor has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements.

FIG. 3 depicts a perspective view of a first support assembly of the surgical retractor system of FIG. 1.

Figure 1:
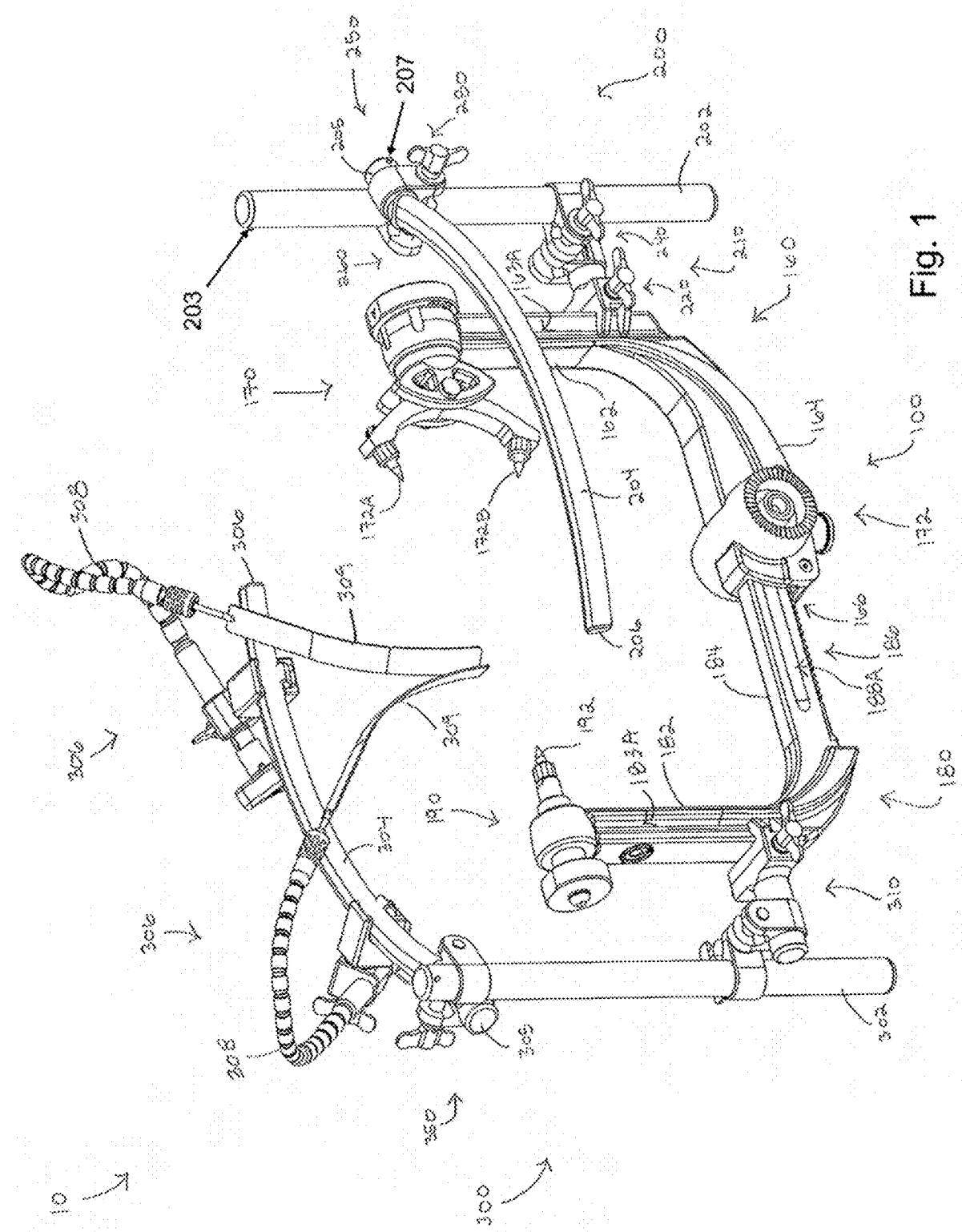
FIG. 1 depicts a perspective view of an exemplary surgical retractor system connected with a head fixation system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description. As will be realized, the invention is capable of other different and obvious aspects, all without departing from the invention. Accordingly, the drawings and descriptions should be regarded as illustrative in nature and not restrictive.

I. Exemplary Surgical Retractor System

Figure 2:
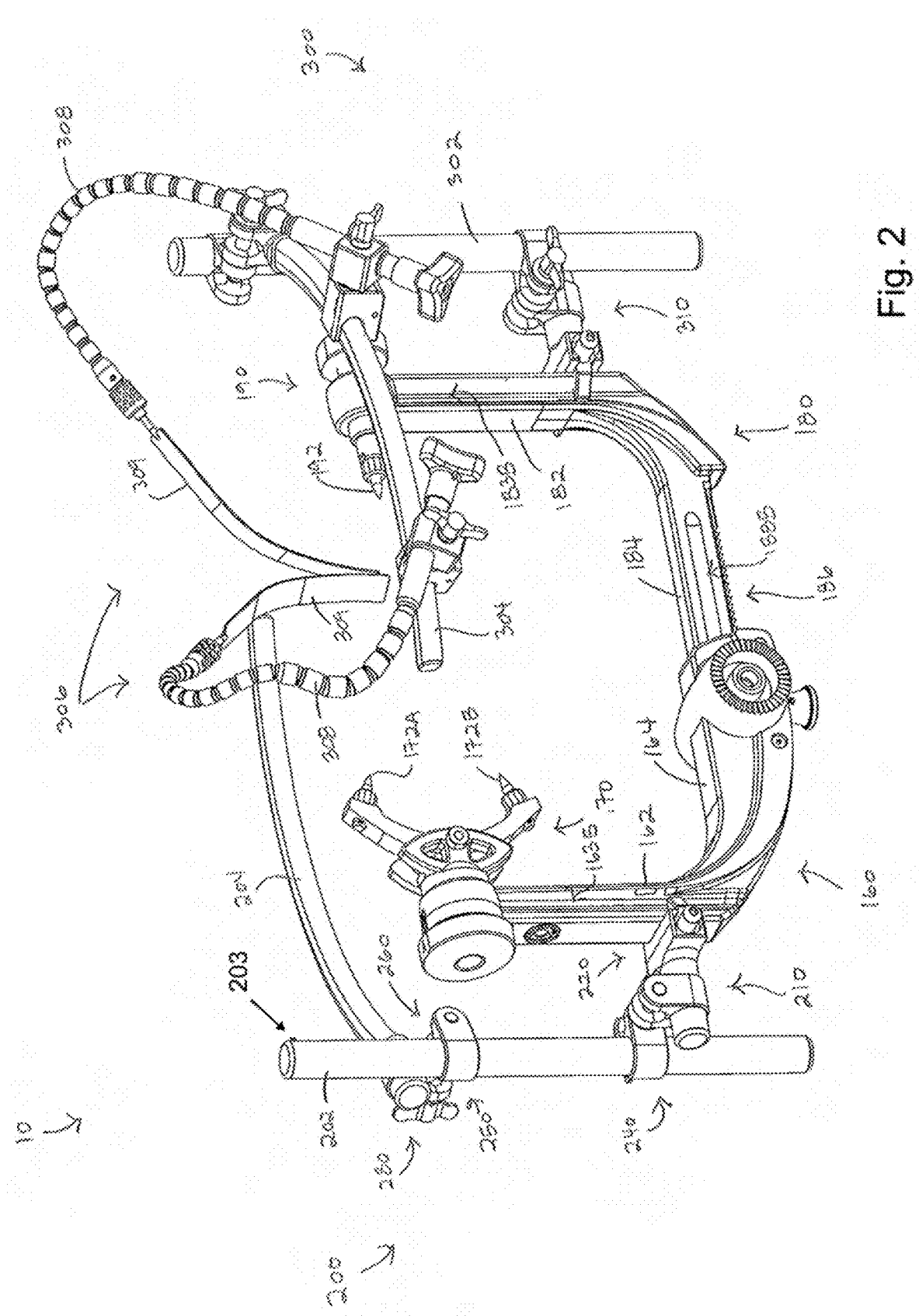
FIG. 2 depicts another perspective view of the combined surgical retractor system and head fixation system of FIG. 1.

FIGS. 1-2 illustrate an exemplary surgical retractor system (10) attached with a head fixation system or stabilization device in the form of a skull clamp (100). Surgical refractor system (10) comprises a first support assembly (200), and a second support assembly (300). Skull clamp (100) includes a first arm (160) and a second arm (180) that each include generally upright portions (162, 182) and generally lateral portions (164, 184). Upright portions (162, 182) each include a rail having grooves or slots (163A, 163B, 183A, 183B) therein with the rails formed on opposite sides of upright portions (162, 182) respectively. First support assembly (200) is selectively coupled with rail of upright portion (162) of first arm (160) via a coupling assembly (210). As will be discussed in more detail below, coupling assembly (210) is vertically slidable or translatable along the rail such that the position of first support assembly (200) may be changed relative to skull clamp (100). Second support assembly (300) is selectively coupled with rail of upright portion (182) of second arm (180) via a coupling assembly (310). As will be discussed in more detail below, coupling assembly (310) is vertically slidable or translatable along the rail such that the position of second support assembly (300) may be changed relative to skull clamp (100). In some other versions, coupling assemblies (210, 310) may connect to other devices, e.g. a surgical table, instead of skull clamp (100). Other devices to which surgical retractor system (10) can connect to via coupling assemblies (210, 310) will be apparent to those of ordinary skill in the art in view of the teachings herein.

Referring to skull clamp (100), lateral portion (184) of second arm (180) includes a plurality of teeth (186) positioned downward or away from where the patient's head would be positioned. Lateral portion (164) of first arm (160) includes a lateral slot (166) that is configured to receive lateral portion (184) of second arm (180) such that arms (160, 180) are slidable relative to one another and such that the relative position of arms (160, 180) with respect to one another may be changed. To achieve the desired alignment of arms (160, 180) when assembling them to form skull clamp (100), a pair of raised guides (not shown) extend from each interior side surface of first arm (160) and engage with a pair of corresponding recessed slots (188A, 188B) formed in each exterior side of lateral portion (184) of second arm (180). A locking device (not shown) functions to engage teeth (186) of second arm (180) to engage arms (160, 180) together in a selective locking fashion; U.S. Pat. Pub. 2014/0135765, entitled "Skull Clamp Opening Apparatus and Method," published May 15, 2014, the disclosure of which is incorporated by reference herein, discloses such a locking device.

As shown in FIGS. 1-2, at a top of upright portions (162, 182) of each arm are pin holder assemblies (170, 190). On second arm (180), there is a single pin holder assembly (190) that holds a single pin (192). On first arm (160), there is a dual pin holder assembly (170) that holds two pins (172A, 172B). Pins (172A, 172B, 192) engage with a patient's head to create the stabilization. Skull clamp (100) also includes an attachment feature (172) that is located on lateral portion (164) of first arm (160). In the present example, attachment feature (172) is configured as a starburst and this is where skull clamp (100) can be attached to other structures, e.g., an operating table via one or more adapters.

A. First Exemplary Support Assembly

FIG. 3 shows first support assembly (200) of surgical retractor system (10). First support assembly (200) comprises first coupling assembly (210), a rod (202), a second coupling assembly (250), and a second rod or an oval-shaped member (204). Rod (202) of first support assembly (200) is coupled to first arm (160) of skull clamp (100) via first coupling assembly (210). As will be discussed in more detail below, rod (202) is rotatable about and movable along multiple axes relative to upright portion (162) of first arm (160). Furthermore, oval-shaped member (204) of first support assembly (200) is coupled to rod (202) via second coupling assembly (250). As will be discussed in more detail below, oval member (204) is rotatable about and movable about multiple axes relative to rod (202) of first support assembly (200).

1. First Coupling Assembly

Figure 4A:
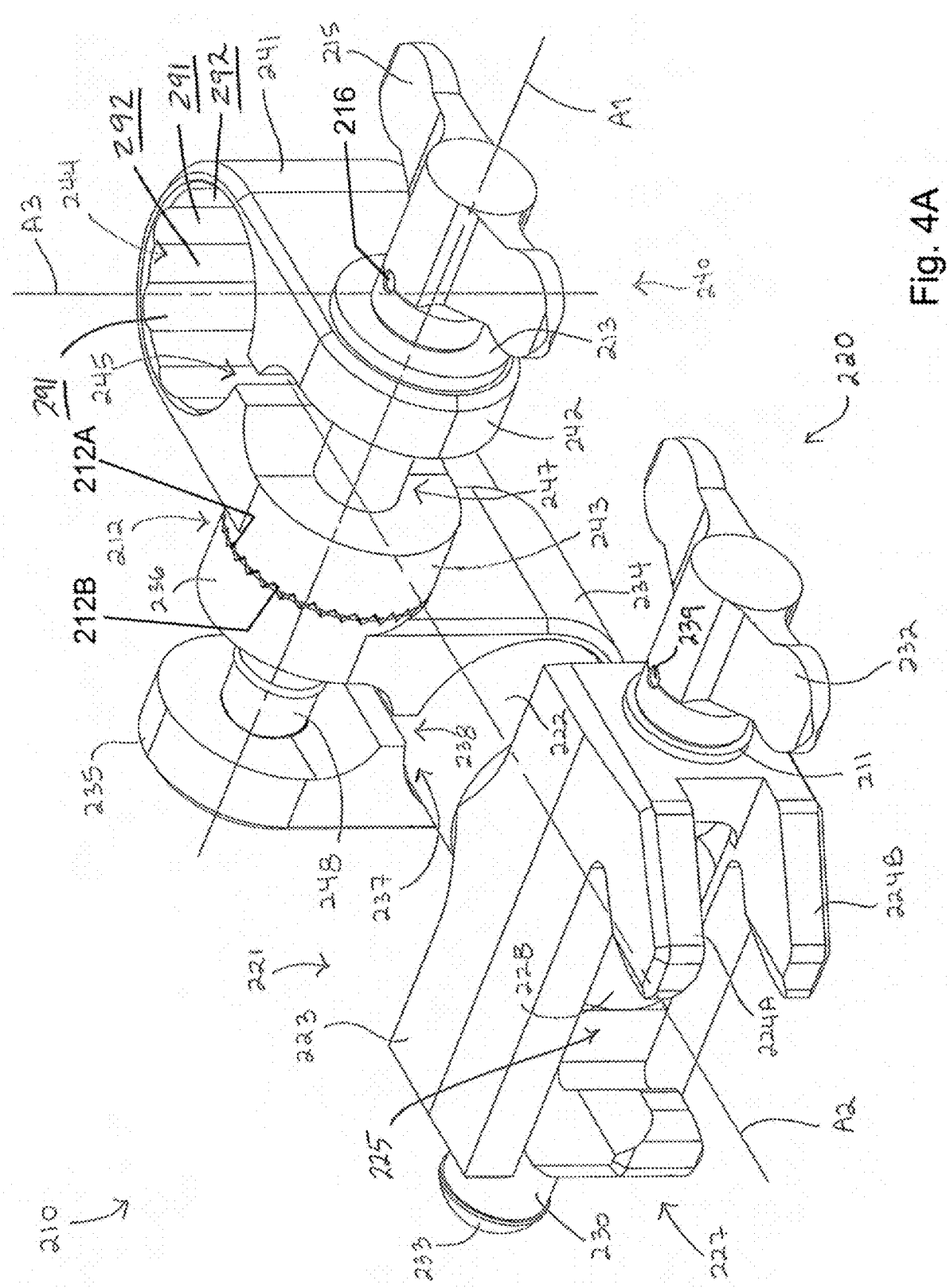
FIG. 4A depicts a perspective view of a first coupling assembly of the surgical retractor system of FIG. 1 that is operable to couple the first support assembly of FIG. 3 to an arm of the head fixation system of FIG. 1.
Figure 5:
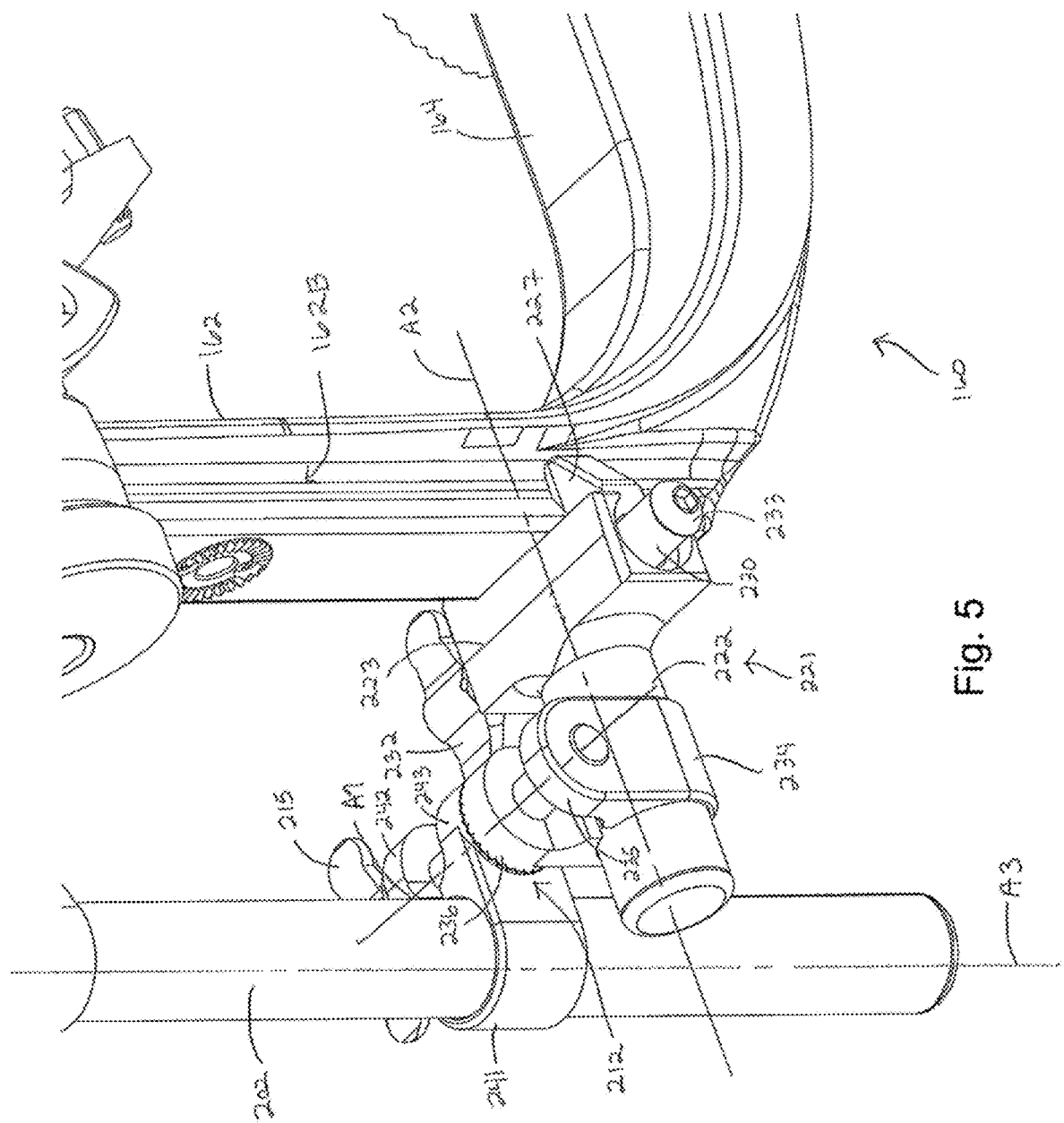
FIG. 5 depicts a detailed perspective view of the first support assembly of FIG. 3, the first coupling assembly of FIG. 4A, and the arm of the head fixation system of FIG. 1.

FIGS. 3, 4A and 5 show an exemplary first coupling assembly (210). First coupling assembly (210) comprises a first portion (220) and a second portion (240) that engage one another via starburst feature (212). First portion (220) and second portion (240) are therefore rotatable relative to one another about a first axis (A1) perpendicular to starburst feature (212). As will be discussed in more detail below, first portion (220) of coupling assembly (210) is coupled to upright portion (162) of first arm (160), while second portion (240) of coupling assembly (210) is coupled to rod (202). Thus it should be understood that starburst feature (212) of coupling assembly (210) enables rod (202) to rotate about first axis (A1), an axis of rotation.

First portion (220) of coupling assembly (210) comprises a body (221) and a resilient member (234). As best seen in FIG. 5, body (221) includes a cylindrical member (222) and a grasping member (223). Cylindrical member (222) extends from grasping member (223). As will be discussed in more detail below, resilient member (234) is configured to slidably and rotatably receive cylindrical member (222) of body (221). Grasping member (223) includes a pair of jaws (224A, 224B) configured to engage the rail of upright portion (162). Grasping member (223) presents a channel (225) which partially extends through grasping member (223) and is configured to slidably receive a jaw (227). Jaw (227) is linearly translatable within channel (225) along an axis defined by channel (225). Jaw (227) is configured to engage the rail of upright portion (162) of skull clamp (100). Thus, it should be understood that jaw (227) and pair of jaws (224A, 224B) are configured to couple with the rail of upright portion (162) of first arm (160) of skull clamp (100). Of course in other versions grasping member (223) can grasp other structures and devices other than a skull clamp like skull clamp (100), e.g. such other structures and devices may include a surgical table among other things. Other structures and devices to which grasping member (223) can be connected with will be apparent to those of ordinary skill in the art in view of the teachings herein.

Jaw (227) includes a cylindrical member (228) having a bore which passes completely there through. An interior surface of the bore presents a plurality of threads. As stated above, channel (225) passes only partially through grasping member (223). Grasping member (223) comprises a bore which passes through the remaining portion of grasping member (223) such that channel (225) and bore define a path which passes completely through grasping member (223). Body (221) includes a threaded member (230) which is rotatably disposed within this path. Threaded member (230) comprises a cylindrical projection nearest the end close to paddle member (232), and this cylindrical projection passes through bore (226). The cylindrical projection is secured to a paddle member (232) via pin (239) that extends through the cylindrical projection and paddle member (232) such that a user may rotate threaded member (230) via paddle member (232). An exterior surface of threaded member (230) presents a plurality of threads. The plurality of threads of the bore of jaw (227) are configured to matingly receive the plurality of threads of the threaded member (230). As discussed above, channel (225) is configured to slidably receive jaw (227); however, jaw (227) is unable to rotate within channel (225). Thus, it should be understood that, rotation of threaded member (230) is configured to cause jaw (227) to slide within channel (225) to thereby cause jaw (227) and pair of jaws (224A, 224B) to selectively engage or disengage the rail of upright portion (162) of skull clamp (100). It should be understood that jaw (227) and pair of jaws (224A, 224B) may be loosened such that first clamping assembly (210) (and consequentially first support assembly (200)) may be moved vertically or translated relative to upright portion (162) of first arm (160) of skull clamp (100). As best seen in FIG. 5, a member (233) is secured to an end of threaded member (230) to thereby limit the amount by which jaw (227) may slide within channel (225) and along threaded member (230). Furthermore, washer member (211) is positioned between paddle member (232) and an exterior surface of grasping member (223) to facilitate rotation of paddle member (232) and threaded member (230).

Resilient member (234) is generally U-shaped. Resilient member (234) comprises a pair of flanges (235, 236) which define a circular bore (237) between them. A slot (238) is defined between flanges (235, 236) within a top portion of circular bore (237) such that flanges (235, 236) may be moved toward and away from one another. Circular bore (237) of resilient member (234) is configured to slidably and rotatably receive cylindrical member (222) of body (221). As discussed in more detail below, rotation of a threaded member (247) of second portion (240) is configured to cause flanges (235, 236) to move toward and away from one another to thereby compress or loosen about cylindrical member (222) respectively. It should be understood that the nature of the coupling between cylindrical member (222) and resilient member (234) will allow rod (202) (and consequentially first support assembly (200)) to move toward and away from first arm (160) and to further rotate about a second axis (A2) defined by cylindrical member (222).

Figure 4B:
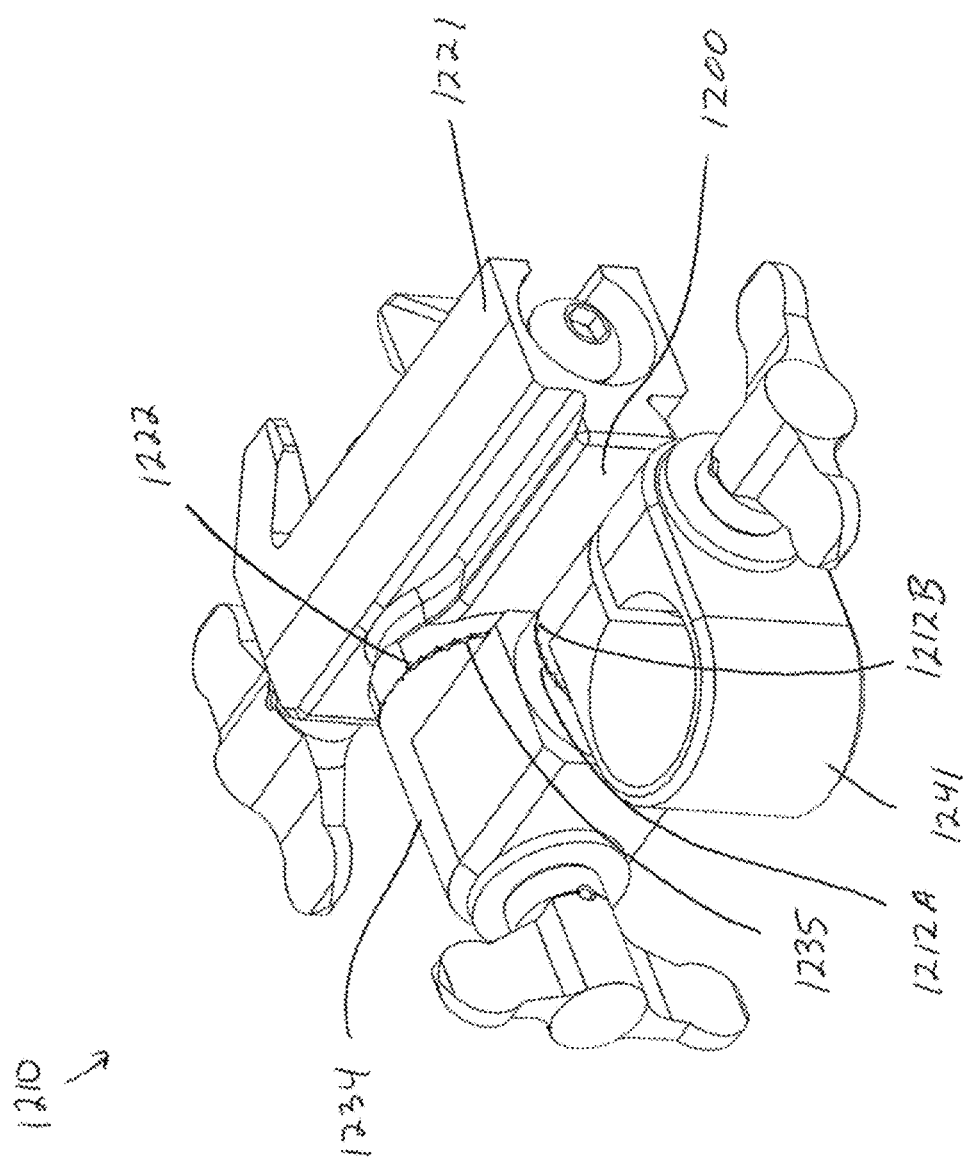
FIG. 4B depicts a perspective view of another exemplary first coupling assembly of the surgical retractor system of FIG. 1 that is operable to couple the first support assembly of FIG. 3 to an arm of the head fixation system of FIG. 1.

Referring to FIG. 4B, an alternate exemplary first coupling assembly (1210) is shown that can be used instead of or in addition to first coupling assembly (210). Many features of first coupling assembly (1210) are the same or similar to first coupling assembly (210). However, one difference is that cylindrical member (222) of first coupling assembly (210) is replaced with starburst feature (1222) in first coupling assembly (1210). Also, resilient member (234) of first coupling assembly (210) is then replaced with adapter (1234) in first coupling assembly (1210). Adapter (1234) comprises starburst feature (1235) that is configured to selectively engage with starburst feature (1222) to selectively connect adapter (1234) with body (1221) of first coupling assembly (1210). Furthermore, adapter (1234) comprises starburst feature (1212A) that is configured to selectively engage starburst feature (1212B) of resilient member (1241), which is similar to resilient member (241) in first coupling assembly (210). Another difference between first coupling assembly (210) and first coupling assembly (1210) is that first coupling assembly (1210) comprises a rail portion (1200) that can be used to connect other devices to body (1221) of first coupling assembly (1210).

Referring to FIG. 4A, circular bore (237) of resilient member (234) comprises a plurality of alternating non-contacting surfaces (291) and contacting surfaces (292) that surround and define the interior perimeter of circular bore (237) the same as what is shown in FIG. 4A for bore (244) of resilient member (241). In some instances, contacting surfaces (292) can be considered ridges while non-contacting surfaces (291) can be considered spacers. As shown in the illustrated version, non-contacting surfaces (291) and contacting surfaces (292) are arcuate or curved surfaces and are concave to different degrees. For instance, non-contacting surfaces (291) have a greater degree of curvature compared to contacting surfaces (292). In some versions, the degree of curvature of contacting surfaces (292) is configured to match the arcuate outer surface of cylindrical member (222). Still in other versions, contacting surfaces (292) can be straight with no curvature at all. Still yet, in some versions surfaces (291, 292) may have the same configuration, in other words the same degree of curvature or both lacking curvature altogether and being straight instead. In other versions, circular bore (237) of resilient member (234) contains just a single continuous curved surface, for instance similar to that shown in FIG. 7B with exemplary resilient member (1280). In yet other versions, non-contacting surfaces (291) and contacting surfaces (292) of circular bore (237) of resilient member (234) are oriented orthogonally to axis A2 rather than parallel with axis A2, for instance similar to that shown in FIG. 7C with exemplary resilient members (2260, 2280). In the illustrated version of FIG. 4A, circular bore (237) comprises about eight contacting surfaces (292). In other versions the number and size of contacting surfaces (292) and non-contacting surfaces (291) can be smaller or larger to provide greater or fewer incidences of contact with cylindrical member (222) and larger or smaller areas of contact with cylindrical member (222). For instance, in some versions there are a maximum of two contacting surfaces (292) within the curved portion of circular bore (237). In still other versions, there are a maximum of three contacting surfaces (292) within the curved portion of circular bore (237). In still other versions, there is an odd number of contacting surfaces (292) within the curved portion of circular bore (237).

Referring to FIGS. 4A and 5, second portion (240) of first coupling assembly (210) comprises a resilient member (241). Resilient member (241) is generally U-shaped. Resilient member (241) comprises a pair of flanges (242, 243) which define a circular bore (244) between them. A slot (245) is defined between flanges (242, 243) within a top portion of circular bore (244) such that flanges (242, 243) may be moved toward and away from one another. Circular bore (244) of resilient member (241) is configured to slidably and rotatably receive rod (202) of first support assembly (200). As discussed in more detail below, rotation of threaded member (247) of second portion (240) is configured to cause flanges (242, 243) to move toward and away from one another to thereby compress or loosen about rod (202). It should be understood that the nature of the coupling between rod (202) and resilient member (241) will allow rod (202) (and consequentially first support assembly (200)) to move vertically relative to first coupling assembly (210) and first arm (160), and to further rotate about a third axis (A3) defined by rod (202) as well as bore (244).

Circular bore (244) of resilient member (241) comprises the same configurations as that describe above with respect to circular bore (237) of resilient member (234). More specifically, circular bore (244) of resilient member (241) comprises a plurality of alternating non-contacting surfaces (291) and contacting surfaces (292) that surround and define the interior perimeter of circular bore (244). In some instances, contacting surfaces (292) can be considered ridges while non-contacting surfaces (291) can be considered spacers. As shown in the illustrated version, non-contacting surfaces (291) and contacting surfaces (292) are arcuate or curved surfaces and are concave to different degrees. For instance, non-contacting surfaces (291) have a greater degree of curvature compared to contacting surfaces (292). In some versions, the degree of curvature of contacting surfaces (292) is configured to match the arcuate outer surface of rod (202). Still in other versions, contacting surfaces (292) can be straight with no curvature at all. Still yet, in some versions surfaces (291, 292) may have the same configuration, in other words the same degree of curvature or both lacking curvature altogether and being straight instead. In other versions, circular bore (244) of resilient member (241) contains just a single continuous curved surface, for instance similar to that shown in FIG. 7B with exemplary resilient member (1280). In yet other versions, non-contacting surfaces (291) and contacting surfaces (292) of circular bore (244) of resilient member (241) are oriented orthogonally to axis A3 rather than parallel with axis A3 as shown in FIG. 4A, for instance similar to that shown in FIG. 7C with exemplary resilient members (2260, 2280). In the illustrated version of FIG. 4A, circular bore (244) comprises about eight contacting surfaces (292). In other versions the number and size of contacting surfaces (292) and non-contacting surfaces (291) can be smaller or larger to provide greater or fewer incidences of contact with rod (202) and larger or smaller areas of contact with rod (202). For instance, in some versions there are a maximum of two contacting surfaces (292) within the curved portion of circular bore (244). In still other versions, there are a maximum of three contacting surfaces (292) within the curved portion of circular bore (244). In still other versions, there is an odd number of contacting surfaces (292) within the curved portion of circular bore (244).

As best seen in FIG. 4A, an exterior surface of flange (236) of resilient member (234) presents a first starburst feature (212A) and an exterior surface of flange (243) of resilient member (241) presents a second starburst feature (212B). First starburst feature (212A) and second starburst feature (212B) together form starburst feature (212). As discussed in more detail below, rotation of threaded member (247) of second portion (240) is configured to cause first feature (212A) and second starburst feature (212B) to engage and/or disengage one another. When engaged, resilient members (234, 241) are connected to one another such that their relative positions are secured or locked.

Each flange (235, 236, 242, 243) of resilient members (234, 241) include a respective opening which passes completely through a respective flange (235, 236, 242, 243). Each opening of each flange (235, 236, 242, 243) is aligned along first axis (A1). A spring (not shown) is positioned between the exterior surface of flange (236) of resilient member (234) and the exterior surface of flange (243) of resilient member (241) to thereby drive resilient member (234) and resilient member (241) away from one another. Threaded member (247) of second portion (240) includes a threaded region (248) at a first end of threaded member (247). An exterior surface of threaded region (248) presents a plurality of threads. An interior surface of the opening of flange (235) of resilient member (234) presents a plurality of threads. Threaded member (247) is configured to pass completely through each opening of each flange (235, 236, 242, 243) of resilient members (234, 241) such that the plurality of threads of threaded region (248) of threaded member (247) matingly engages the plurality of threads of the opening of flange (235) of resilient member (234). A second end of threaded member (247) is secured to a paddle member (215) via pin (216) that extends through an end portion of threaded member (247) such that a user may rotate threaded member (247) via paddle member (215). Paddle member (215) is sized such that it is not able to pass through the opening of flange (242) of resilient member (241). Thus it should be understood that rotation of threaded member (247) about first axis (A1) is configured to cause (a) movement of flanges (235, 236) of resilient member (234) toward or away from one another to selectively clamp, lock, or secure to cylindrical member (222); (b) movement of flanges (242, 243) of resilient member (241) toward or away from one another to selectively clamp, lock, or secure to rod (202); and (c) engagement or disengagement of first starburst feature (212A) of flange (236) of resilient member (234) and second starburst feature (212B) of flange (243) of resilient member (241). Furthermore, washer member (213) is positioned between paddle member (215) and an exterior surface of flange (242) of resilient member (241) to facilitate rotation of paddle member (215) and threaded member (247).

From the discussion above, it should be understood that, among other things, coupling assembly (210) allows rod (202) and oval-shaped member (204) of first support assembly (200) to rotate about first axis (A1), second axis (A2), and third axis (A3); to slide longitudinally along second axis (A2) and third axis (A3); and to slide vertically and horizontally relative to upright portion (162) of first arm (160) of skull clamp (100).

2. Second Coupling Assembly

Figure 6:
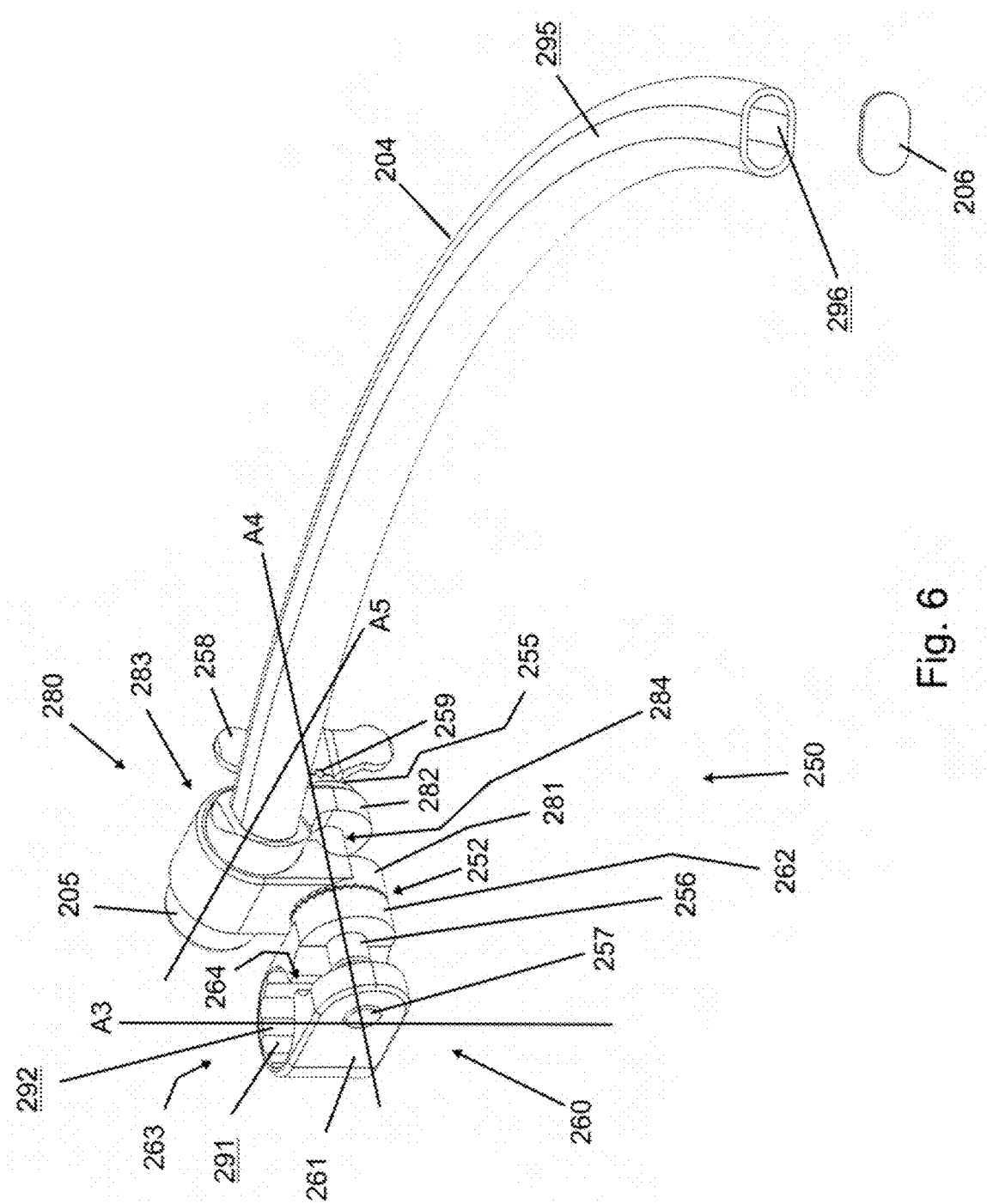
FIG. 6 depicts a perspective view of a second coupling assembly operable to couple an oval member of the first support assembly of FIG. 3 with a rod of the first support assembly of FIG. 3.
Figure 7A:
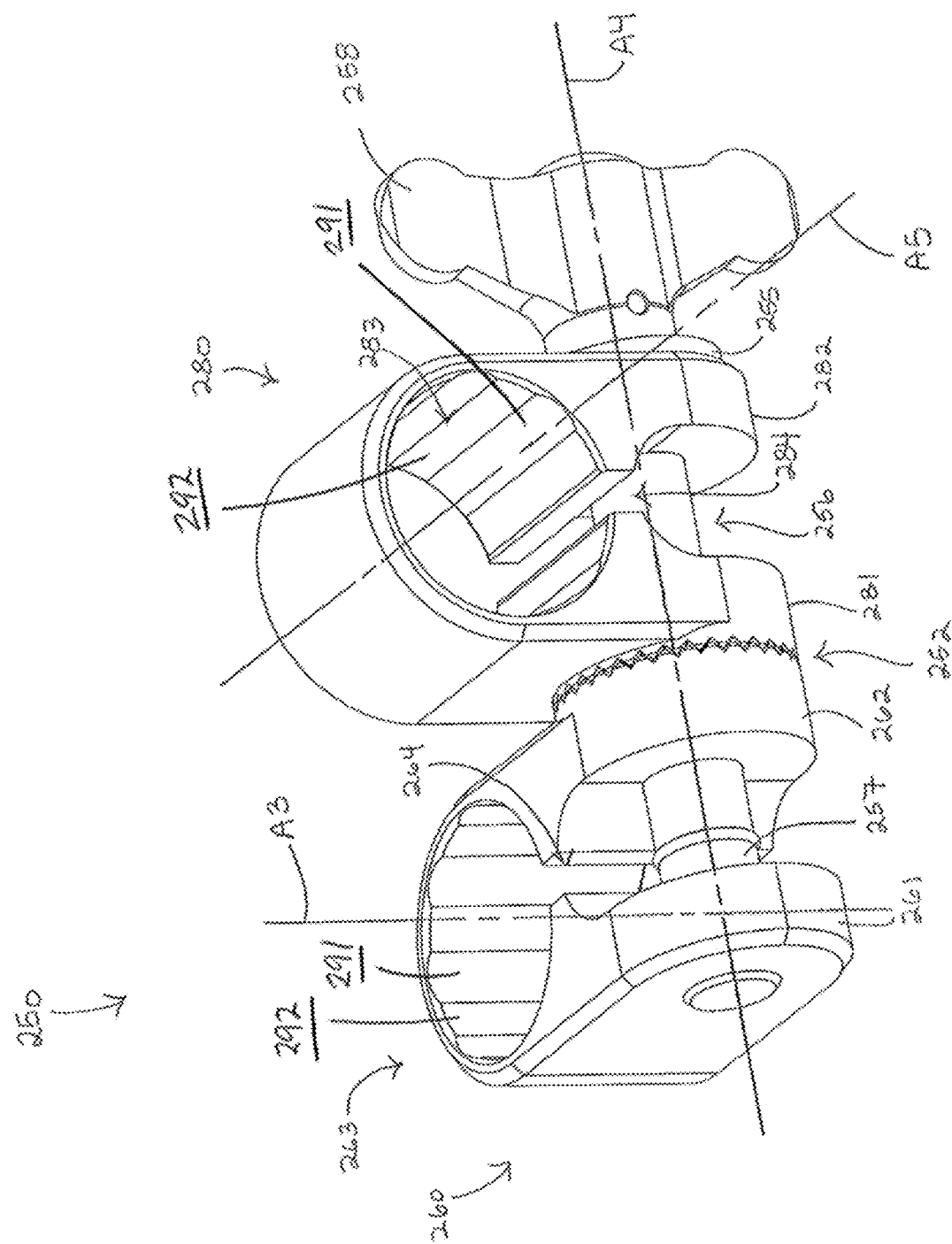
FIG. 7A depicts a perspective view of the second coupling assembly of FIG. 6.

FIGS. 6 and 7A show second coupling assembly (250). Second coupling assembly (250) comprises a pair of resilient members (260, 280) which engage one another via a starburst feature (252). Resilient member (260) and resilient member (280) are therefore rotatable relative to one another about a fourth axis (A4) perpendicular to starburst feature (252). As will be discussed in more detail below, resilient member (260) of coupling assembly (250) is slidably and rotatably coupled to rod (202); while resilient member (280) of coupling assembly (250) is slidably and rotatably coupled to oval-shaped member (204). Thus it should be understood that starburst feature (252) of coupling assembly (250) enables oval-shaped member (204) to rotate about fourth axis (A4) defined by coupling assembly (250).

Resilient member (260) is generally U-shaped. Resilient member (260) comprises a pair of flanges (261, 262) which define a circular bore (263) between them. A slot (264) is defined between flanges (261, 262) within a top portion of circular bore (263) such that flanges (261, 262) may be moved toward and away from one another. Circular bore (263) of resilient member (260) is configured to slidably and rotatably receive rod (202) of first support assembly (200). As discussed in more detail below, rotation of a threaded member (256) is configured to cause flanges (261, 262) to move toward and away from one another to thereby compress or loosen about rod (202) respectively. It should be understood that the nature of the coupling between rod (202) and resilient member (260) will allow coupling assembly (250) to move vertically relative to rod (202) and to further rotate about third axis (A3) which, as discussed above, is defined by rod (202). As will discussed in more detail below, because oval-shaped member (204) is coupled with coupling assembly (250), oval-shaped member (204) may be moved vertically relative to rod (202) and to further rotate about rod (202).

Circular bore (263) of resilient member (260) comprises the same configuration as that describe above with respect to circular bore (237) of resilient member (234). More specifically, circular bore (263) of resilient member (260) comprises a plurality of alternating non-contacting surfaces (291) and contacting surfaces (292) that surround and define the interior perimeter of circular bore (263). In some instances, contacting surfaces (292) can be considered ridges while non-contacting surfaces (291) can be considered spacers. As shown in the illustrated version, non-contacting surfaces (291) and contacting surfaces (292) are arcuate or curved surfaces and are concave to different degrees. For instance, non-contacting surfaces (291) have a greater degree of curvature compared to contacting surfaces (292). In some versions, the degree of curvature of contacting surfaces (292) is configured to match the arcuate outer surface of rod (202). Still in other versions, contacting surfaces (292) can be straight with no curvature at all. Still yet, in some versions surfaces (291, 292) may have the same configuration, in other words the same degree of curvature or both lacking curvature altogether and being straight instead. In other versions, circular bore (263) of resilient member (260) contains just a single continuous curved surface, for instance similar to that shown in FIG. 7B with exemplary resilient member (1280). In yet other versions, non-contacting surfaces (291) and contacting surfaces (292) of circular bore (263) of resilient member (260) are oriented orthogonally to axis A3 rather than parallel with axis A3 as shown in FIG. 6, for instance similar to that shown in FIG. 7C with exemplary resilient members (2260, 2280). In the illustrated version, circular bore (263) comprises about eight contacting surfaces (292). In other versions the number and size of contacting surfaces (292) and non-contacting surfaces (291) can be smaller or larger to provide greater or fewer incidences of contact with rod (202) and larger or smaller areas of contact with rod (202). For instance, in some versions there are a maximum of two contacting surfaces (292) within the curved portion of circular bore (263). In still other versions, there are a maximum of three contacting surfaces (292) within the curved portion of circular bore (263). In still other versions, there is an odd number of contacting surfaces (292) within the curved portion of circular bore (263).

As shown in FIG. 6, a first end of oval-shaped member (204) is coupled with a cylindrical member or adapter (205) such that oval-shaped member (204) extends from cylindrical member (205) at an oblique angle relative to a fifth axis (A5) defined by cylindrical member (205) or bore (283) of resilient member (280). A second end of oval-shaped member (204) is closed off by a cap (206), which is shown exploded from oval-shaped member (204) in FIG. 6 to illustrate that in the present example, oval-shaped member (204) is a hollow yet rigid structure. Oval-shaped member (204) comprises an oval cross-section with a straight portions on each side. These straight portions of the cross-section define smooth flat surfaces (295, 296) in the oval-shaped member (204). As will be discussed in more detail below, oval-shaped member (204) is capable of having accessories selectively coupled thereto. Furthermore, oval-shaped member (204) is configured to provide or act as an ergonomic support rest for a surgeon or other medical personnel to rest their one or more arms or hands during a medical procedure. Oval-shaped member (204) is also configured to provide or act as an ergonomic structure for stabilizing or steadying a surgeon or other medical personnel's one or more hands or arms during a medical procedure. In the present example, the non-round cross sectional shape of oval-shaped member (204) distributes pressure over a larger area when used as an arm/hand support/rest. This makes oval-shaped member (204) more ergonomic and comfortable to use as a support/rest compared to, e.g. a structure with a circular cross sectional profile or other profiles that create or have pressure points due to not distributing the weight of the person's arm/hand over a larger surface area. While the present example describes the support structure or support rest as having a shape that is elongated with a curve and with an oval shaped profile, other non-round shapes may be used. Other such shapes may include, but are not limited to, a curved elongated member having an egg shaped profile, a teardrop shaped profile, a rectangular shaped profile with rounded edges, or a square shaped profile with rounded edges.

As shown in the illustrated version, oval-shaped member (204) is curved or arcuate. In the present example as illustrated in FIG. 1, oval-shaped members (204, 304) are curved and positioned such that they both curve away from what would be the field of view for a head surgery or medical procedure. More specifically, oval-shaped member (204) is positioned on the same side of skull clamp (100) as attachment feature (172) that is configured to attach skull clamp (100) to e.g. a table adapter that connects with an operating table for instance. With this arrangement, a patient's head would be positioned in skull clamp (100) and the patient's body would extend in the direction opposite to the direction attachment feature (172) faces. For ease of reference, the patient will be considered to extend in a distal direction, the opposite direction to that being the proximal direction. As shown, oval-shaped member (204) curves in the proximal direction thereby not obstructing the field of view of the surgery or procedure site. Oval-shaped member (304) is positioned on the opposite side as oval-shaped member (204), and furthermore curves in the distal direction thereby also no obstructing the field of view of the surgery or procedure site. Thus in some versions, the two oval-shaped members (204, 304) curve in opposite manners or directions. And furthermore, the curvature of each of the two oval-shaped members (204, 304) when connected to the overall apparatus is such that they curve in a manner that follows the contour of the patient's head positioned in the field of view below the oval-shaped members (204, 304).

As shown in FIG. 1, one exemplary configuration uses one oval-shaped member (304) for attaching one or more accessories (306)—in the present example shown as flexible arms (308) with tools (309) or blades connected thereto. Flexible arms (308) and tools (309) or blades can also be considered and referred to as retractor arms. Then, still referring to FIG. 1, a second oval-shaped member (204) is used and is configured for providing a support rest or stabilizing rest or steadying rest for a medical personnel's one or more arms or hands. In view of the teachings herein, other arrangements and uses for oval-shaped members (204, 304) will be apparent to those of ordinary skill in the art. For instance, the direction of curvature for oval-shaped member (204, 304) can be changed by rotating oval-shaped members (204, 304) and their connected cylindrical members (205, 305). Furthermore, in some versions one oval-shaped member can be used as a hand rest with another oval-shaped member having skin hooks attached to it. Still yet, in some versions two or more oval-shaped members (204, 304) can be attached to one rod (202, 302).

Resilient member (280) is generally U-shaped. Resilient member (280) comprises a pair of flanges (281, 282) which define a circular bore (283) between them. A slot (284) is defined between flanges (281, 282) within a top portion of circular bore (283) such that flanges (281, 282) may be moved toward and away from one another. Circular bore (283) of resilient member (280) is configured to slidably and rotatably receive cylindrical member (205) coupled to oval-shaped member (204). As discussed in more detail below, rotation of threaded member (256) is configured to cause flanges (281, 282) to move toward and away from one another to thereby compress or loosen about cylindrical member (205). It should be understood that the nature of the coupling between cylindrical member (205) and resilient member (280) will allow oval-shaped member (204) to move longitudinally along fifth axis (A5) and to further rotate about fifth axis (A5).

Circular bore (283) of resilient member (280) comprises the same configuration as that describe above with respect to circular bore (237) of resilient member (234). More specifically, circular bore (283) of resilient member (280) comprises a plurality of alternating non-contacting surfaces (291) and contacting surfaces (292) that surround and define the interior perimeter of circular bore (283). In some instances, contacting surfaces (292) can be considered ridges while non-contacting surfaces (291) can be considered spacers. As shown in the illustrated version, non-contacting surfaces (291) and contacting surfaces (292) are arcuate or curved surfaces and are concave to different degrees. For instance, non-contacting surfaces (291) have a greater degree of curvature compared to contacting surfaces (292). In some versions, the degree of curvature of contacting surfaces (292) is configured to match the arcuate outer surface of cylindrical member (205). Still in other versions, contacting surfaces (292) can be straight with no curvature at all. Still yet, in some versions surfaces (291, 292) may have the same configuration, in other words the same degree of curvature or both lacking curvature altogether and being straight instead. In other versions, circular bore (283) of resilient member (280) contains just a single continuous curved surface, for instance similar to that shown in FIG. 7B with exemplary resilient member (1280). In yet other versions, non-contacting surfaces (291) and contacting surfaces (292) of circular bore (263) of resilient member (280) are oriented orthogonally to axis A5 rather than parallel with axis A5 as shown in FIG. 7A, for instance similar to that shown in FIG. 7C with exemplary resilient members (2260, 2280). In the illustrated version, circular bore (283) comprises about eight contacting surfaces (292). In other versions the number and size of contacting surfaces (292) and non-contacting surfaces (291) can be smaller or larger to provide greater or fewer incidences of contact with cylindrical member (205) and larger or smaller areas of contact with cylindrical member (205). For instance, in some versions there are a maximum of two contacting surfaces (292) within the curved portion of circular bore (283). In still other versions, there are a maximum of three contacting surfaces (292) within the curved portion of circular bore (283). In still other versions, there is an odd number of contacting surfaces (292) within the curved portion of circular bore (283).

As best seen in FIG. 6, an exterior surface of flange (262) of resilient member (260) presents a first starburst feature and an exterior surface of flange (281) of resilient member (280) presents a second starburst feature. First starburst feature and second starburst feature together form starburst feature (252). As discussed in more detail below, rotation of threaded member (256) is configured to cause first starburst feature and second starburst feature to engage and disengage one another.

Each flange (261, 262, 281, 282) of resilient members (260, 280) include a respective opening which passes completely through a respective flange (261, 262, 281, 282). Each opening of each flange (261, 262, 281, 282) is aligned along fourth axis (A4). A spring (not shown) is positioned between the exterior surface of flange (261) of resilient member (260) and the exterior surface of flange (281) of resilient member (280) to thereby drive resilient member (260) and resilient member (280) away from one another. Threaded member (256) of second portion (240) includes a threaded region (257) at a first end of threaded member (256). An exterior surface of threaded region (257) presents a plurality of threads. An interior surface of the opening of flange (261) of resilient member (260) presents a plurality of threads. Threaded member (256) is configured to pass completely through each opening of each flange (261, 262, 281, 282) of resilient members (260, 280) such that the plurality of threads of threaded region (257) of threaded member (256) matingly engages the plurality of threads of the opening of flange (261) of resilient member (260). A second end of threaded member (256) is secured to a paddle member (258) via pin (259) that extends through threaded member (256) and paddle member (258) such that a user may rotate threaded member (256) via paddle member (258). Paddle member (258) is sized such that it is not able to pass through the opening of flange (282) of resilient member (280). Thus it should be understood that rotation of threaded member (256) about fourth axis (A4) is configured to cause (a) movement of flanges (261, 262) of resilient member (260) toward or away from one another to selectively clamp, lock, or secure to rod (202); (b) movement of flanges (281, 282) of resilient member (280) toward or away from one another to selectively clamp, lock, or secure to cylindrical member (205); and (c) engagement or disengagement of first starburst feature of flange (262) of resilient member (260) and second starburst feature of flange (281) of resilient member (280). Furthermore, washer member (255) is positioned between paddle member (258) and an exterior surface of flange (282) of resilient member (280) to facilitate rotation of paddle member (258) and threaded member (256).

It should be understood that second coupling assembly (250) allows oval-shaped member (204) of first support assembly (200) to rotate about third axis (A3), fourth axis (A4), and fifth axis (A5); to slide longitudinally along fifth axis (A5); and to slide vertically along third axis (A3).

Figure 7B:
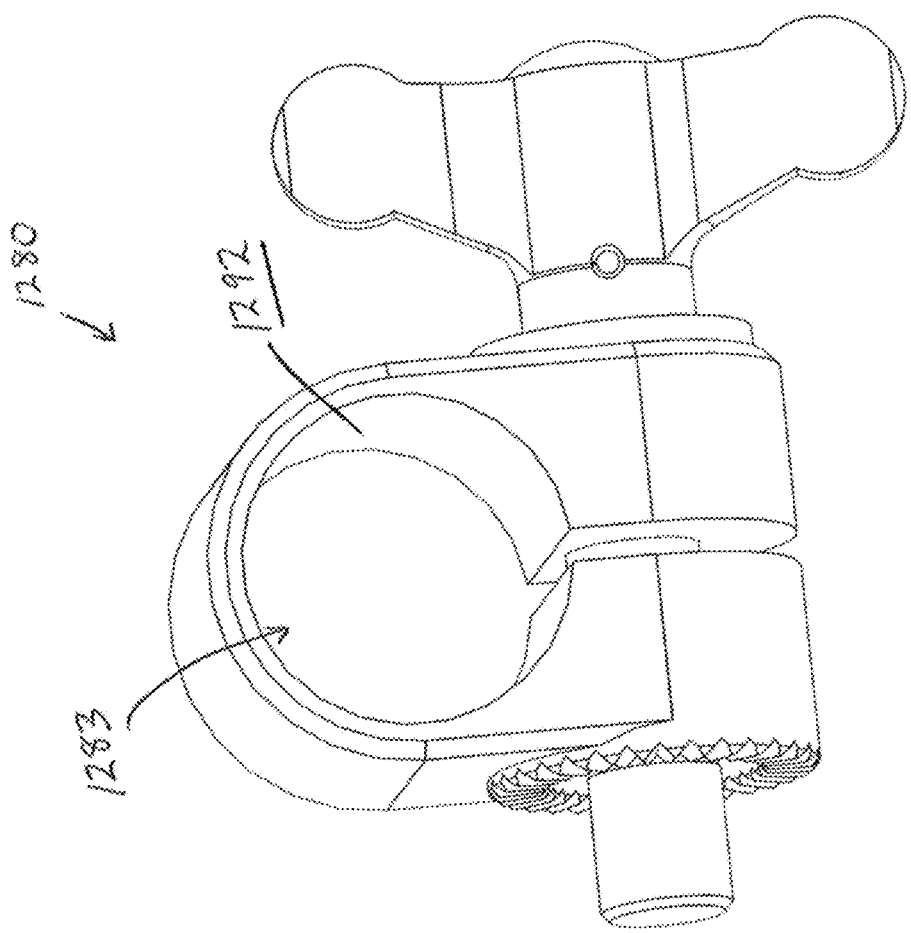
FIG. 7B depicts a perspective view of a portion of another exemplary second coupling assembly.
Figure 7C:
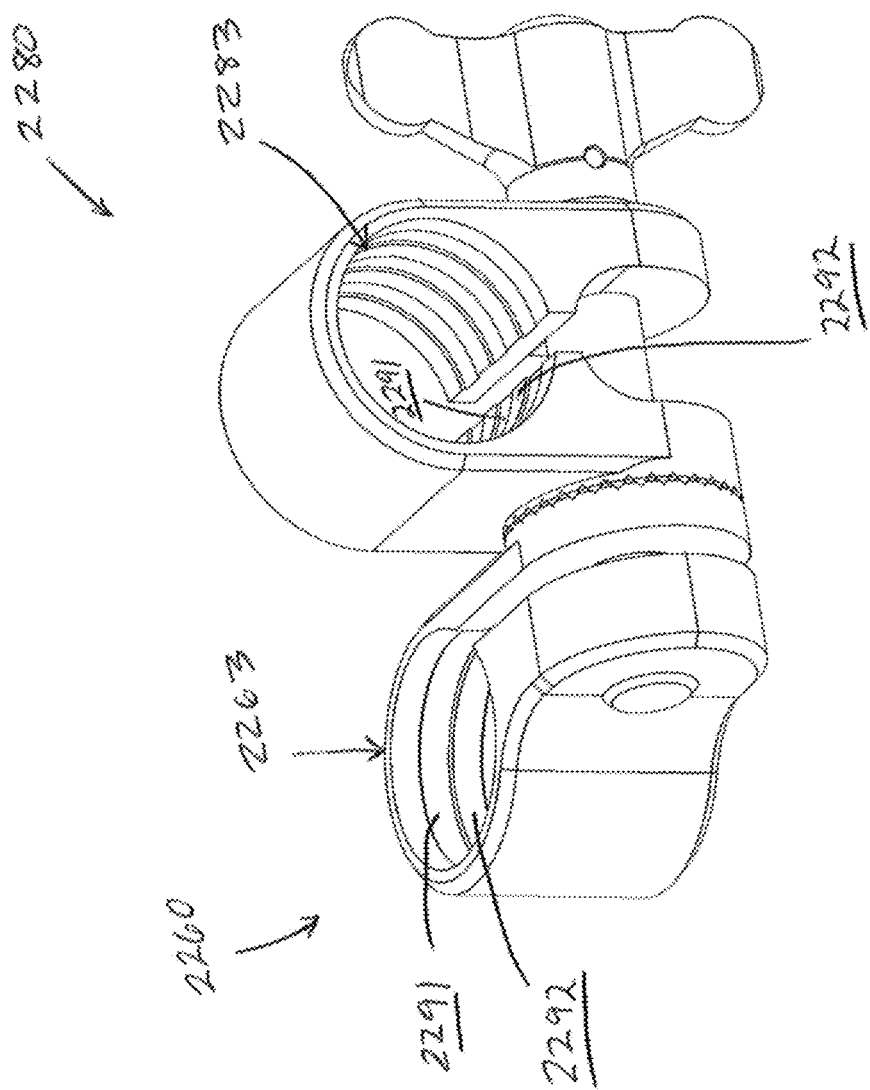
FIG. 7C depicts a perspective view of another exemplary second coupling assembly.

Referring to FIGS. 7A, 7B, and 7C, exemplary resilient members (260, 280, 1280, 2260, 2280) are illustrated. These resilient members show alternative interior surface configurations for the respective circular bores of each resilient member. For instance, resilient members (260, 280) depict circular bores (263, 283) having interior surfaces with alternating non-contacting surfaces (291) and contacting surfaces (292) that are oriented parallel with the axis that extends through the respective circular bores. Resilient members (2260, 2280) depict circular bores (2263, 2283) having interior surfaces with alternating non-contacting surfaces (2291) and contacting surfaces (2292) that are oriented orthogonally with the axis that extends through the respective circular bores. Resilient member (1280) depicts circular bore (1283) having a continuous contacting surface (1292). In various versions of retractor system (10) any described resilient member can be configured or modified to have any of the configurations shown in FIGS. 7A-7C. Furthermore, retractor system (10) can be configured or modified such that more than one configuration of resilient member is used within the same retractor system (10). Other ways to configure and modify resilient members and retractor system (10) will be apparent to those of ordinary skill in the art in view of the teachings herein.

Referring to FIGS. 1 and 3, first rod (202) further comprises a stop pin (203). As illustrated, first rod (202) extends through bore (263) of coupling assembly (250). When installing coupling assembly (250) onto rod (202), slot (264) is aligned with stop pin (203) such that coupling assembly (250) can be slid onto rod (202) without coupling assembly (250) contacting stop pin (203) and thus preventing placement of coupling assembly (250) onto rod (202). Once coupling assembly (250) is on rod (202), coupling assembly (250) can be rotated such that stop pin (203) is no longer aligned with slot (264). With this configuration, when making adjustments, rod (202) can be slid downward without passing through or separating from coupling assembly (250) as stop pin (203) will contact or interfere with resilient member (260) of coupling assembly (250).

Similarly, second rod or oval-shaped member (204) further comprises a stop pin (207). As illustrated, second rod (204) extends through bore (283) of coupling assembly (250). When installing coupling assembly (250) onto rod (204), slot (284) is aligned with stop pin (207) such that coupling assembly (250) can be slid onto rod (204) without coupling assembly (250) contacting stop pin (207) and thus preventing placement of coupling assembly (250) onto rod (204). Once coupling assembly (250) is on rod (204), coupling assembly (250) can be rotated such that stop pin (207) is no longer aligned with slot (284). With this configuration, when making adjustments, rod (204) can be slid away from coupling assembly (250) without passing through or separating from coupling assembly (250) as stop pin (207) will contact or interfere with resilient member (280) of coupling assembly (250).

B. Second Exemplary Support Assembly

Figure 8:
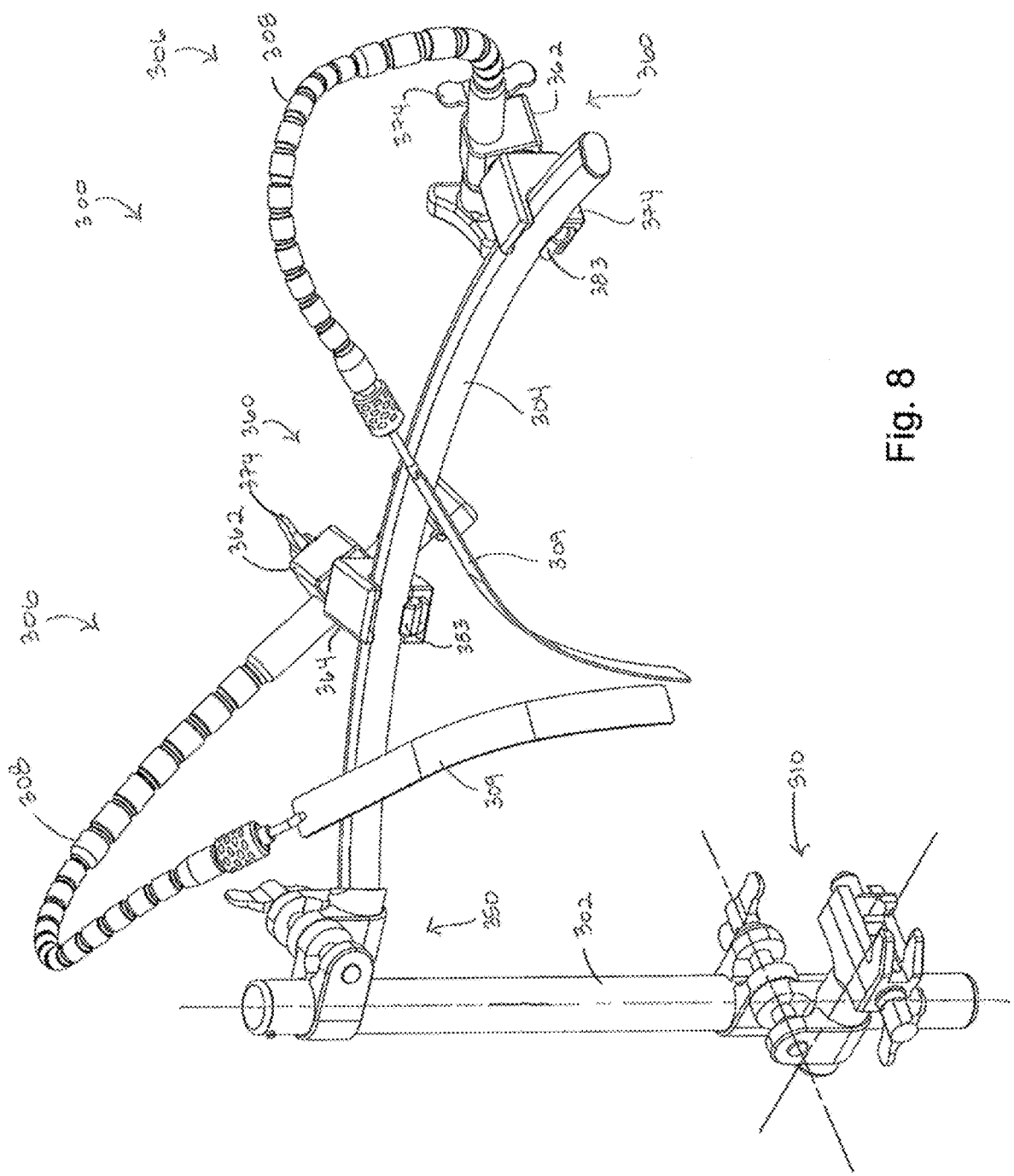
FIG. 8 depicts a perspective view of a second support assembly of the surgical retractor system of FIG. 1.

FIG. 8 shows second support assembly (300). Second support assembly (300) comprises coupling assembly (310), a rod (302), a coupling assembly (350), and an oval-shaped member (304) that is substantially similar to oval-shaped member (204). Rod (302) of second support assembly (300) is coupled to second arm (180) via coupling assembly (310). As will be discussed in more detail below, rod (302) is rotatable about multiple axes relative to upright portion (182) of second arm (180) of skull clamp (100). Furthermore, oval-shaped member (304) of second support assembly (300) is coupled to rod (302) via coupling assembly (350). As will be discussed in more detail below, oval member (304) is rotatable about multiple axes relative to rod (302) of second support assembly (300).

It should be understood that, coupling assembly (310) is configured to operate substantially similar to coupling assembly (210) discussed above. In particular, coupling assembly (310) couples rod (302) of second support assembly (300) to upright portion (182) of second arm (180). Furthermore, coupling assembly (310) allows rod (302) and oval-shaped member (304) of second support assembly (300) to rotate about multiple axes; to slide longitudinally along multiple axes; and to slide vertically and horizontally relative to upright portion (182) of second arm (180).

It should be understood that, coupling assembly (350) is configured to operate substantially similar to coupling assembly (250) discussed above. In particular, coupling assembly (350) couples rod (302) of second support assembly (300) to oval-shaped member (304) of second support assembly (300). Furthermore, coupling assembly (350) allows oval-shaped member (304) of second support assembly (300) to rotate about multiple axes; to slide longitudinally relative to a portion of oval-shaped member (304); and to slide vertically relative to rod (302).

As shown in FIG. 8, second support assembly (300) further comprises accessories (306) coupled to oval-shaped member (304) via third coupling assemblies (360). Accessories (306) of the present example comprise a retractor arm which comprises flexible arm (308) and tool (309). An exemplary flexible arm is disclosed in U.S. Pat. Pub. 2014/0275799, entitled "Flexible Arm and Method of Using", published Sep. 18, 2014, the disclosure of which is incorporated by reference herein. Flexible arms (308) are configured to selectively couple to tools (309), e.g. in the present example retractor blades. Furthermore, other types of accessories can be attached with oval-shaped members (204, 304) in addition to or instead of retractor arms, e.g. skin hooks.

FIGS. 9-11B show third coupling assembly (360). Third coupling assembly (360) comprises a first body portion (362) and a second body portion (364) which engage one another via starburst feature (366). First body portion (362) and second body portion (364) are rotatable relative to one another about a sixth axis (A6) perpendicular to starburst feature (366). As will be discussed in more detail below, first body portion (362) of third coupling assembly (360) is coupled to accessory (306), while second body portion (364) of third coupling assembly (360) is coupled to oval-shaped member (304). Thus it should be understood that starburst feature (366) of third coupling assembly (360) enables accessory (306) to rotate about sixth axis (A6).

First body portion (362) includes a bore which passes completely through first body portion (362) perpendicular to sixth axis (A6). A first end of accessory (306) is positioned within the bore and is secured therein such that accessory (306) is secured to first body portion (362). First body portion (362) further presents another bore which passes completely through first body portion (362) along sixth axis (A6), and a rod (370) is rotatably disposed within this bore.

Rod (370) extends from first body portion (362) and is secured to a paddle member or knob (374) via a pin that extends through rod (370) and paddle member (374) such that a user may rotate rod (370) via paddle member (374). Paddle member (374) is sized such that it is not able to pass through first body portion (362). A spring (373) is positioned between first body portion (362) and second body portion (364) to thereby bias second body portion (364) away from first body portion (362). Rod (370) is configured to pass completely through first body portion (362) and threadably engage a non-rotatable piston member (not shown) within second body portion (364). Rotation of rod (370) about sixth axis (A6) will cause linear movement of the piston member within second body portion (364). Furthermore, it should be understood that rotation of rod (370) in a first direction would cause first body portion (362) and second body portion (364) to move toward one another, overcoming the spring bias. Rotation of rod (370) in a second direction would cause first body portion (362) and second body portion (364) to move away from one another at least in part because of the bias of spring (373). Also, an exterior surface of first body portion (362) presents a first starburst feature (366A) and an exterior surface of second body portion (364) presents a second starburst feature (366B). Thus, it should further be understood that rotation of rod (370) about sixth axis (A6) will cause first starburst feature (366A) and second starburst feature (366B) to engage or disengage thereby locking or unlocking rotational movement between first and second body portions (362, 364).

Second body portion (364) comprises a locking member (379). Locking member (379) is positioned within recess (367). Locking member (379) is rotatably secured within recess (367) via a pin (380) such that locking member is rotatable about pin (380). Locking member (379) comprises a pair of arms (381A, 381B). The piston member is rotatably secured to arms (381A, 381B) such that longitudinal movement of the piston member along sixth axis (A6), from rotation of paddle (374) and rod (370), will cause locking member (379) to rotate from a locked position to an unlocked position and vice versa depending on the direction of rotation of paddle (374) and rod (370). When locking member (379) rotates to a locked position, lip (383) of locking member (379) is rotated upwards or towards oval-shaped member (304) to securely hold oval-shaped member (304). Similarly, when locking member (379) rotates to an unlocked position, lip (383) of locking member (379) is rotated downwards or away from oval-shaped member (304). It is this driving of locking member (379) toward the locked and unlocked positions that respectively "locks" or "unlocks" oval-shaped member (304) within recess (367). Once locking member (379) is in the locked position, further rotation of paddle (374) causes first and second body portions (362, 364) to engage at starburst features (366A, 366B). Thus when fully tightened, both locking member (379) and first and second body portions (362, 364) are locked.

Figure 9:
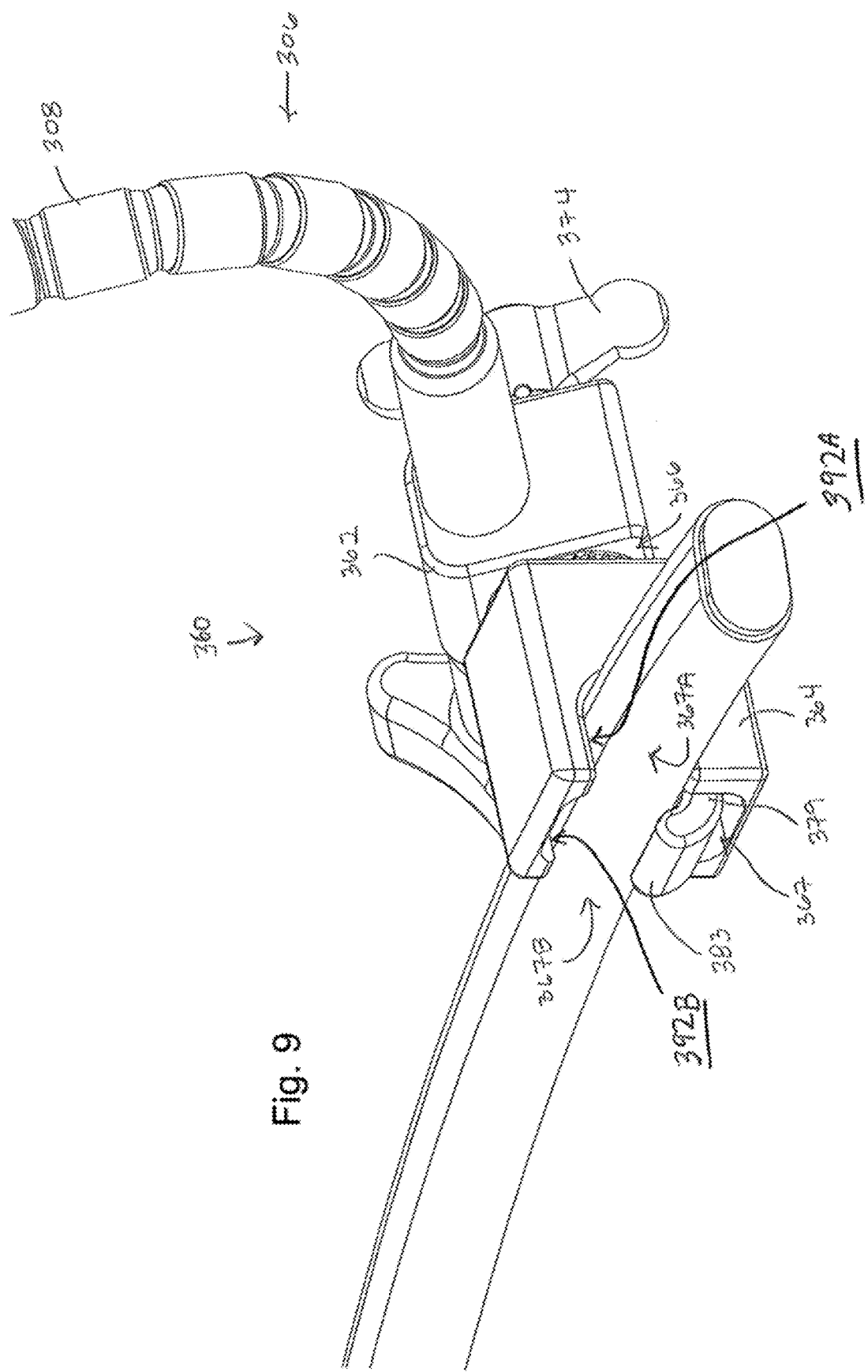
FIG. 9 depicts a perspective view of a third coupling assembly operable to couple an accessory, e.g. a retractor arm, to an oval member of the second support assembly of FIG. 8.
Figure 10:
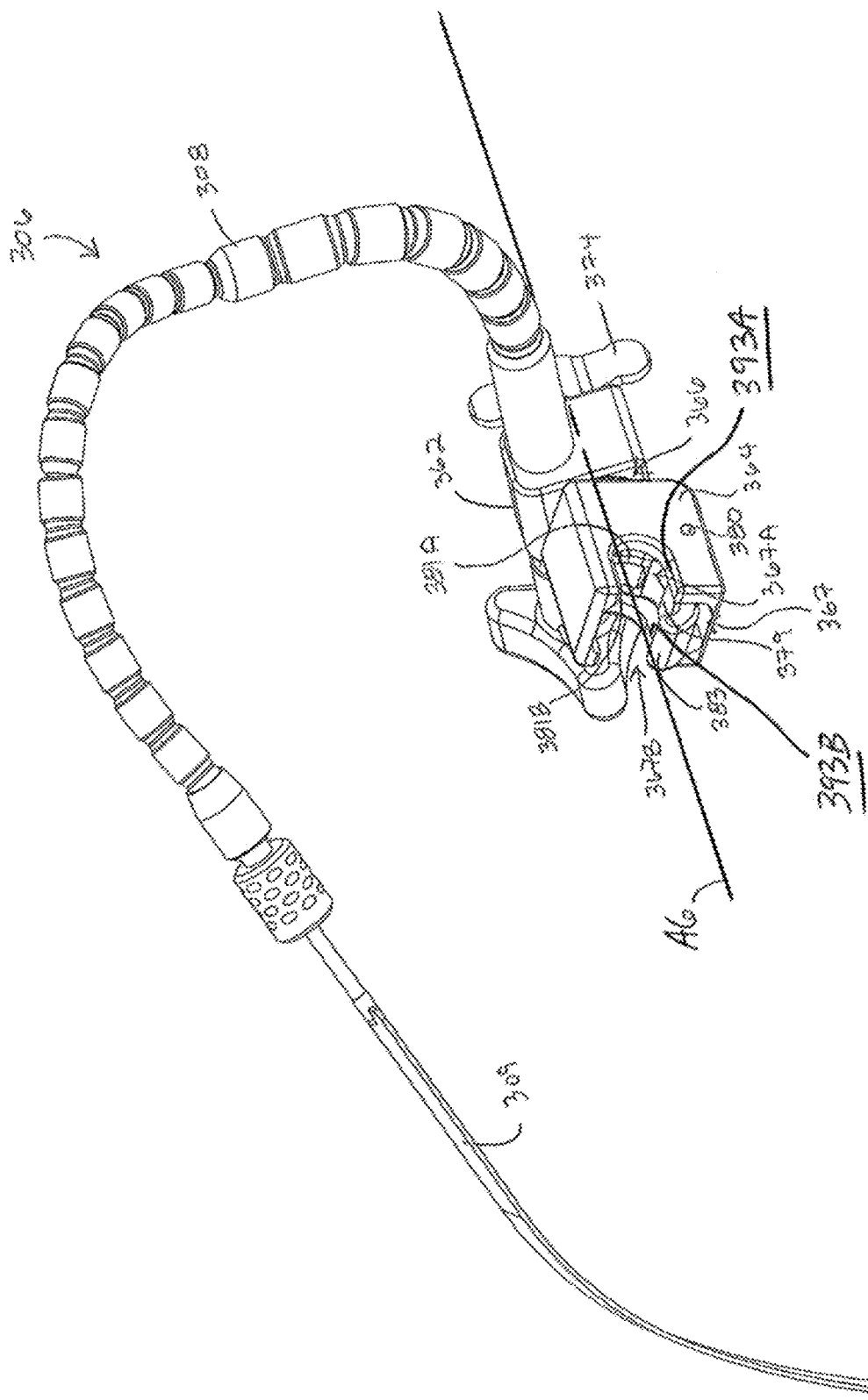
FIG. 10 depicts a perspective view of the third coupling assembly and retractor arm of FIG. 9.
Figure 11A:
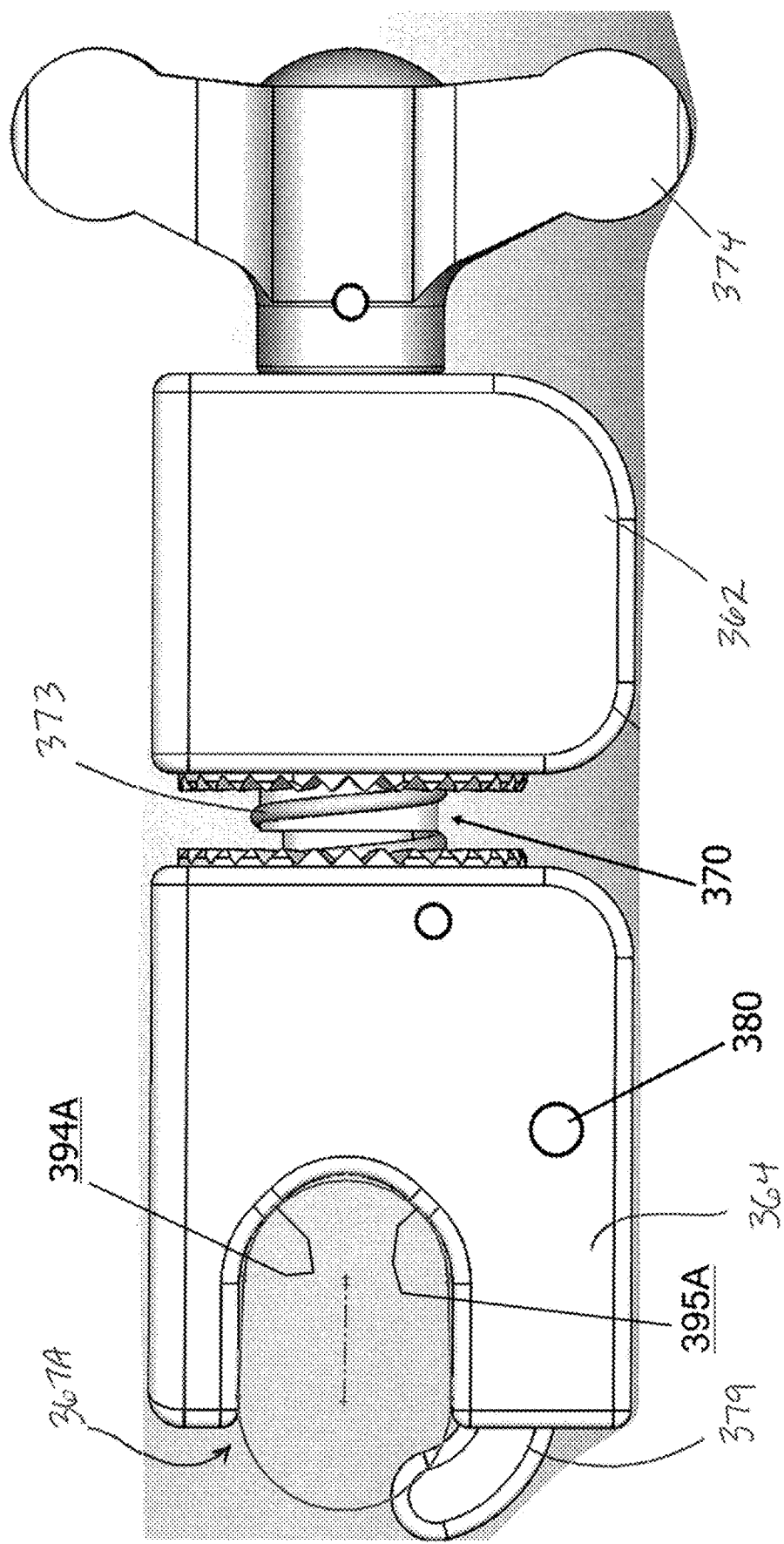
FIGS. 11A and 11B depict side views of the third coupling assembly of FIG. 9 with an oval-shaped member shown in phantom.
Figure 11B:
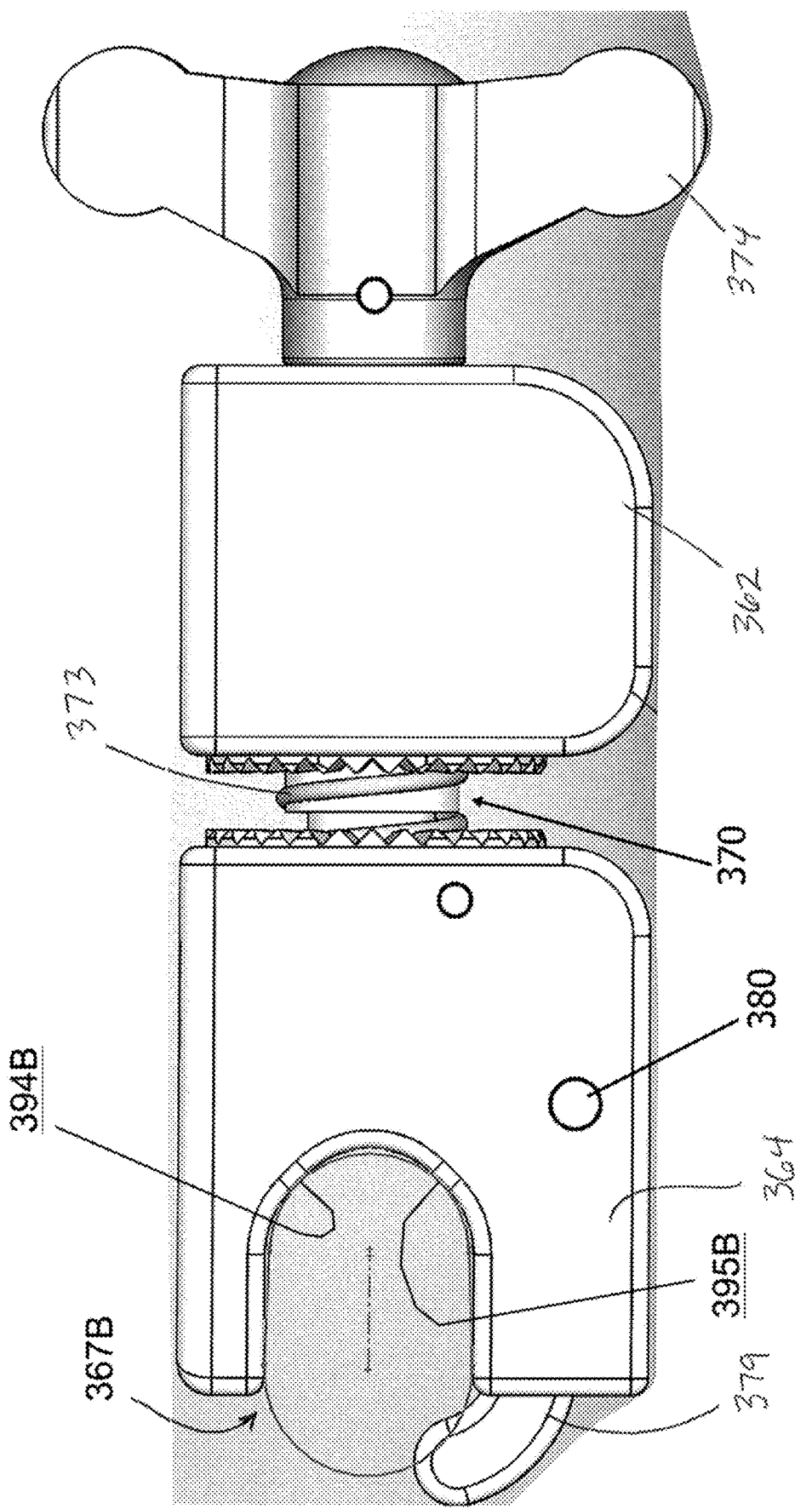

As best seen in FIGS. 9-11B, a pair of slots (367A, 367B) are formed in exterior side surfaces of second body portion (364) and open up into recess (367). Slots (367A, 367B) are formed such that they are capable of receiving oval-shaped member (304) as shown. Slots (367A, 367B) comprise upper flat or straight surfaces (392A, 392B) as shown in FIG. 9 and lower flat or straight surfaces (393A, 393B) as shown in FIG. 10. Referring to FIGS. 11A and 11B, slots (367A, 367B) further comprise multiple diagonal flat or straight surfaces (394A, 395A, 394B, 395B). In the present example, as best understood from FIGS. 9-11B, each slot (367A, 367B) comprises two or more of the diagonal flat or straight surfaces (394A, 395A, 394B, 395B). With this configuration, when locking member (379) is unlocked, oval shaped member (204, 304) can be positioned within slots (367A, 367B) with relative ease as there is some degree of play or freedom of movement of oval-shaped member (204, 304) within slots (367A, 367B). With oval-shaped member (204, 304) within slots (367A, 367B), when locking member (379) is moved to the locked position, lip (383) contacts oval-shaped member (204, 304) and pushes oval-shaped member (204, 304) in an inward and upwards direction or diagonal direction. This causes oval-shaped member (204, 304) to contact upper flat surfaces (392A, 392B) as well as diagonal flat surfaces (394A, 395A, 394B, 395B) of slots (367A, 367B). Thus, in the present example, when locked in place, at least seven surfaces of third coupling assembly (360) contact oval-shaped member (204, 304), namely three surfaces of each slot (367A, 367B) along with the surface of locking member (379). In some versions, when in the locked position, oval-shaped members (204, 304) are secured by contact with only lip (383) of locking member (379) and contact with diagonal surfaces (394A, 395A, 394B, 395B) of slots (367A, 367B). In such versions, oval-shaped members (204, 304) are secured without necessarily contacting upper flat surfaces (392A, 392B) or lower flat surfaces (393A, 393B). Thus in these versions, when locked in place, at least five surfaces of coupling assembly (360) contact oval-shaped member (204, 304), namely two diagonal surfaces (394A, 394B, 394B, 395B) of each slot (367A, 367B) along with the surface of locking member (379).

With the addition of diagonal flat surfaces (394A, 394B, 394B, 395B) within slots (367A, 367B), the play or freedom of movement is minimized or even eliminated when oval-shaped member (204, 304) is in the clamped or locked position. In some versions, when in the locked position, oval-shaped member (204, 304) may not contact bottom flat surfaces (393A, 393B) due to the inward and upward force on oval-shaped member (204, 304) from locking member (379). In some other versions, oval-shaped member (204, 304) may contact bottom flat surfaces (393A, 393B) when oval-shaped member is in the locked position. Again, by incorporating diagonal flat surfaces into slots (367A, 367B), greater tolerances may be available in manufacturing oval-shaped members (204, 304) and third coupling assemblies (360) without sacrificing a secure lock or clamp on oval-shaped rod (204, 304) that has minimal to no play or freedom of movement. Other modifications concerning the shape and configuration of slots (367A, 367B), third coupling assembly (360) generally, and oval-shaped members (204, 304) will be apparent to those of ordinary skill in the art in view of the teachings herein.

In the illustrated version, the locking mechanism for locking and unlocking oval-shaped members (204, 304) can be considered using a prism structure with an oval-shaped member (204, 304). For instance, the two diagonal flat surfaces (394A, 394B, 394B, 395B) within each slot (367A, 367B) can represent half of a prism structure. Thus the diagonal flat surfaces (394A, 394B, 394B, 395B) tangentially contact adjacent oval-shaped member (204, 304) to aid in securing or locking third coupling assembly (360) to oval-shaped member (204, 304). In the present example, the points of contact between coupling assembly (360) and oval-shaped members (204, 304) are minimized to reduce or eliminate play or freedom of movement of oval-shaped members (204, 304) when clamped or locked. Otherwise stated, third coupling assembly (360) can be viewed as having a maximum of two diagonal flat or straight surfaces (394A, 394B, 394B, 395B) in each curved portion defining slots (367A, 367B) of coupling assembly (360). In some other versions, though, third coupling assembly (360) may have greater or fewer than two diagonal flat or straight surfaces within each curved portion of third coupling assembly (360). Again, other modifications concerning the shape and configuration of slots (367A, 367B), third coupling assembly (360) generally, and oval-shaped members (204, 304) will be apparent to those of ordinary skill in the art in view of the teachings herein.

In using third coupling assembly (360) to connect to oval-shaped member (204, 304), beginning with third coupling assembly (360) disconnected from oval-shaped member (204, 304), paddle member (374) is rotated to cause locking member (379) to rotate about pin (380) to an open or unlocked position. For ease, this could also be accomplished by manually forcing first body portion (362) and second body portion (364) together to overcome spring (373), without necessarily rotating paddle member (374), and thereby cause locking member (379) to open. At this point, third coupling assembly (360) can be engaged with oval-shaped member (204, 304) by fitting oval-shaped member (204, 304) within slots (367A, 367B) and intersecting recess (367) of second body portion (364). From this point, paddle member (374) is rotated to cause locking member (379) to rotate about pin (380) to a locked position. In instances where spring (373) was overcome manually, without rotating paddle wheel (374) to release locking member (379) and position oval-shaped member (204, 304) within slots (367A, 367B) and recess (367), once oval-shaped member (204, 304) is positioned, at least one of first and second body portions (362, 364) is released and spring (373) returns to its uncompressed or less compressed state thereby causing locking member (379) to rotate to a locked position. From this point further tightening of paddle member (374) cause first and second body portions (362, 364) to move closer together, with spring (373) compressing until the point where starburst feature (366) engages and locks the relative position of first body portion (362) and second body portion (364). Also, before engagement of starburst feature (366), the rotational position of first body portion (362) relative to second body portion (364) can be adjusted. After third coupling assembly (360) is fully secured, to make further adjustments or remove third coupling assembly (360) from oval-shaped member (204, 304) the reverse steps are performed.

Based on the description above regarding connecting third coupling assembly (360) with oval-shaped member (304), it should be understood that in some instances, second body portion (364) is connectable with oval-shaped member (304) by pushing the locking member (379) onto oval-shaped member (304) from a direction that is orthogonal to the length of oval-shaped member (304). In such instances, as mentioned above, the spring bias between second body portion (364) and first body portion (362) is temporarily overcome by the force of pushing second body portion (364) onto oval-shaped member (304). This force also drives the piston member away from oval-shaped member (304) allowing locking member (379) to rotate open to receive oval-shaped member (304). Once oval-shaped member (304) is within recess (367), the spring bias is no longer overcome and the piston member advances toward oval-shaped member (304) allowing locking member (379) to rotate closed to retain oval-shaped member (304) within recess (367). In this arrangement, third coupling assembly (360) can make an audible click or snap when connecting to oval-shaped member (304).

In an exemplary use of surgical retractor system (10), a user attaches coupling assembly (210) to a stabilization device, e.g. skull clamp (100). As mentioned above, coupling assembly (210) defines first and second axes of rotation. The user further attaches rod (202) with coupling assembly (210). As mentioned above, rod (202) is rotatably adjustable about the first and second axes of rotation. The user further attaches coupling assembly (250) to rod (202). As mentioned above, coupling assembly (250) defines third and fourth axes of rotation. The user further attaches second rod or oval-shaped member (204) with coupling assembly (250). As mentioned above, oval-shaped member (204) is rotatably adjustable about the third and fourth axes of rotation. In some other uses, greater or fewer steps may be performed when using surgical retractor system (10) as will be apparent to those of ordinary skill in the art in view of the teachings herein.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of any claims that may be presented and is understood not to be limited to the details of structure and operation shown and described in the specification and drawings.

I claim:

1. A surgical retractor system for use in a medical procedure, said surgical retractor system comprises:
   (a) a skull clamp configured to stabilize a head of a patient;
   (b) a first rod;
   (c) a second rod, comprising an elongated member having a curved shape along a length of the elongated member, wherein the elongated member with the curved shape defines an arc, wherein a cross-sectional profile of the second rod comprises opposite flat sides and opposite arcuate sides extending between the flat sides;
   (d) a first coupling assembly operable to selectively and adjustably couple the first rod with the skull clamp, wherein the first coupling assembly defines a first axis of rotation and a second axis of rotation, wherein the first rod is rotatably adjustable about the first axis of rotation and the second axis of rotation, wherein rotation of the first rod about a select one or both of the first axis of rotation and the second axis of rotation adjusts a position of the first rod relative to the skull clamp; and
   (e) a second coupling assembly operable to selectively and adjustably couple the second rod with the first rod, wherein the second coupling assembly defines a third axis of rotation and a fourth axis of rotation, wherein the second rod is rotatably adjustable about the third axis of rotation and the fourth axis of rotation, wherein rotation of the second rod about a select one or both of the third axis of rotation and the fourth axis of rotation adjusts a position of the second rod relative to the first rod.

2. The surgical retractor system of claim 1, wherein the second coupling assembly defines a fifth axis of rotation, wherein the second rod is rotatably adjustable about the fifth axis of rotation.

3. The surgical retractor system of claim 2, wherein rotation of the second rod about the fifth axis of rotation adjusts an angle of the flat sides of the second rod relative to the first rod.

4. The surgical retractor system of claim 1, wherein the first coupling assembly is translatable along the skull clamp to adjust the position of the first coupling assembly relative to the skull clamp.

5. The surgical retractor system of claim 1, wherein the second coupling assembly is translatable along the first rod to adjust the position of the second coupling assembly relative to the first rod.

6. The surgical retractor system of claim 1, wherein the first coupling assembly and the second coupling assembly define a common axis of translation, wherein the first rod is translatable along the axis of translation to adjust the position of the first rod relative to the first coupling assembly and the second coupling assembly.

7. The surgical retractor system of claim 1, wherein the first rod extends through a first bore of the second coupling assembly, wherein the first rod comprises a stop pin that prevents the first rod from separating from the bore during adjustment of the surgical retractor system.

8. The surgical retractor system of claim 1, wherein the second rod extends through a second bore of the second coupling assembly, wherein the second rod comprises a stop pin that prevents the second rod from separating from the second bore during adjustment of the surgical retractor system.

9. The surgical retractor system of claim 1, wherein the second rod is hollow.

10. The surgical retractor system of claim 1, wherein the second coupling assembly comprises:
    (a) a first resilient member comprising a first pair of flanges which define a first bore therebetween, wherein the first bore is operable to selectively and adjustably receive the first rod, wherein each flange of the first pair of flanges are operable to move toward and away from one another to thereby increase or decrease engagement between the first bore and the first rod;
    (b) a second resilient member comprising a second pair of flanges which define a second bore therebetween, wherein the second bore is operable to selectively and adjustably receive the second rod, wherein each flange of the second pair of flanges are operable to move toward and away from one another to thereby increase or decrease engagement between the second bore and the second rod; and
    (c) wherein the first resilient member and the second resilient member are selectively securable to one another via a starburst feature.

11. The surgical retractor system of claim 1, wherein the first coupling assembly comprises a first bore that receives the first rod, wherein the second coupling assembly comprises a second bore that receives the first rod, wherein the first and second bores have an interior perimeter comprising at least one contacting surface selectively engaging the first rod and at least one non-contacting surface not engaging the first rod, wherein the at least one non-contacting surface is curved and the at least one contacting surface is straight.

12. The surgical retractor system of claim 1, further comprising a third coupling assembly operable to selectively and adjustably couple an accessory with the second rod such that the accessory is movable along the length of the elongated member of the second rod, wherein the third coupling assembly is connectable with the second rod from a direction that is orthogonal to the length of the elongated member of the second rod.

13. The surgical retractor system of claim 12, wherein the third coupling assembly comprises a body portion comprising a pair of slots to selectively receive the second rod, wherein each slot of the pair of slots comprises a curved surface and at least one straight surface.

14. A surgical retractor system for use in a medical procedure, said surgical retractor system comprises:
   (a) a skull clamp configured to stabilize a head of a patient;
   (b) a first rod;
   (c) a second rod having a cross-sectional profile, wherein the cross-sectional profile of the second rod is oval shaped comprising opposite flat sides and opposite arcuate sides extending between the flat sides;
   (d) a first coupling assembly operable to selectively and adjustably couple the first rod with a skull clamp, wherein the first coupling assembly defines a first axis of rotation and a second axis of rotation, wherein the first rod is rotatably adjustable about the first axis of rotation and the second axis of rotation, wherein rotation of the first rod about a select one or both of the first axis of rotation and the second axis of rotation adjusts a position of the first rod relative to the skull clamp; and
   (e) a second coupling assembly operable to selectively and adjustably couple the second rod with the first rod, wherein the second coupling assembly defines a third axis of rotation and a fourth axis of rotation, wherein the second rod is rotatably adjustable about the third axis of rotation and the fourth axis of rotation, wherein rotation of the second rod about a select one or both of the third axis of rotation and the fourth axis of rotation adjusts a position of the second rod relative to the first rod.

15. A surgical retractor system for use in a medical procedure, said surgical retractor system comprises:
   (a) a skull clamp configured to stabilize a head of a patient;
   (b) a first rod;
   (c) a second rod comprising an elongated member having a curved shape along a length of the elongated member, wherein the elongated member with the curved shape defines an arc;
   (d) a first coupling assembly operable to selectively and adjustably couple the first rod with a skull clamp, wherein the first coupling assembly defines a first axis of rotation and a second axis of rotation, wherein the first rod is rotatably adjustable about the first axis of rotation and the second axis of rotation, wherein rotation of the first rod about a select one or both of the first axis of rotation and the second axis of rotation adjusts a position of the first rod relative to the skull clamp; and
   (e) a second coupling assembly operable to selectively and adjustably couple the second rod with the first rod, wherein the second coupling assembly defines a third axis of rotation, a fourth axis of rotation, and a fifth axis of rotation, wherein the second rod is rotatably adjustable about the third axis of rotation, the fourth axis of rotation, and the fifth axis of rotation, wherein rotation of the second rod about a select one or more of the third axis of rotation, the fourth axis of rotation, and the fifth axis of rotation adjusts a position of the second rod relative to the first rod, wherein the rotatable adjustability of the second rod about each of the third, fourth, and fifth axes permits rotation of the second rod by at least 360 degrees.

* * * * *